(12) United States Patent
Krinninger et al.

(10) Patent No.: US 11,357,596 B2
(45) Date of Patent: Jun. 14, 2022

(54) MEDICAL HOLDING ARM FOR INCORPORATION INTO A SURGICAL NAVIGATION SYSTEM

(71) Applicant: Brainlab Robotics GmbH, Munich (DE)

(72) Inventors: Maximilian Krinninger, Weßling-Oberpfaffenhofen (DE); Stephan Nowatschin, Munich (DE)

(73) Assignee: Brainlab Robotics GmbH, Munich (DE)

( * ) Notice: Subject to any disclaimer, the term of this patent is extended or adjusted under 35 U.S.C. 154(b) by 428 days.

(21) Appl. No.: 16/336,597

(22) PCT Filed: Sep. 13, 2017

(86) PCT No.: PCT/EP2017/072965
§ 371 (c)(1),
(2) Date: Mar. 26, 2019

(87) PCT Pub. No.: WO2018/054729
PCT Pub. Date: Mar. 29, 2018

(65) Prior Publication Data
US 2019/0223976 A1 Jul. 25, 2019

(30) Foreign Application Priority Data

Sep. 26, 2016 (DE) .................... 10 2016 118 123.4

(51) Int. Cl.
*A61B 90/50* (2016.01)
*A61B 1/00* (2006.01)
(Continued)

(52) U.S. Cl.
CPC .......... *A61B 90/50* (2016.02); *A61B 1/00149* (2013.01); *B25J 1/02* (2013.01); *B25J 13/089* (2013.01); *A61B 2090/508* (2016.02)

(58) Field of Classification Search
CPC ................ A61B 1/00149; A61B 90/50; A61B 2090/508; A61B 34/70; A61B 2017/0039;
(Continued)

(56) References Cited

U.S. PATENT DOCUMENTS

2005/0209614 A1 9/2005 Fenter et al.
2014/0039517 A1 2/2014 Bowling et al.
2015/0252940 A1 9/2015 Goodwin et al.

FOREIGN PATENT DOCUMENTS

DE       195 26 915 A1   2/1997
DE   10 2014 016 823 A1   5/2016
(Continued)

*Primary Examiner* — Anh T Dang
(74) *Attorney, Agent, or Firm* — BakerHostetler

(57) ABSTRACT

A holding device for medical purposes holds an attached device. The holding device has a proximal end for attaching the holding device to a base and a distal end for receiving the attached device. The holding device also has a first arm segment and a second arm segment. The first arm segment is connected to a first joint and the second arm segment is connected to a second joint. Each joint is releasable or lockable. The holding device further has an operator control device for releasing and/or locking the first or second joint for placing the holding device in a desired pose. The holding device also has a controller for controlling the holding device and at least one receiver for electromagnetic radiation connected to the controller for transmitting signals to the controller based on received electromagnetic signals of a surgical navigation system.

19 Claims, 12 Drawing Sheets

(51) Int. Cl.
*B25J 1/02* (2006.01)
*B25J 13/08* (2006.01)

(58) Field of Classification Search
CPC .... A61B 2017/00314; A61B 2090/571; A61B 2034/2051; B25J 1/02; B25J 13/089
See application file for complete search history.

(56) References Cited

FOREIGN PATENT DOCUMENTS

| | | |
|---|---|---|
| DE | 10 2014 019 752 A1 | 5/2016 |
| DE | 10 2017 111 296 B3 | 8/2018 |
| EP | 1 216 651 A1 | 6/2002 |
| EP | 1 854 425 A1 | 11/2007 |
| EP | 1 958 587 A1 | 8/2008 |
| EP | 2 821 024 A1 | 1/2015 |
| EP | 2 965 874 A2 | 1/2016 |
| WO | 2016/114834 A2 | 7/2016 |
| WO | 2017/025607 A1 | 2/2017 |

MEDICAL HOLDING ARM FOR INCORPORATION INTO A SURGICAL NAVIGATION SYSTEM

CROSS-REFERENCE TO RELATED APPLICATIONS

This application is a National Stage of International Patent App. No. PCT/EP2017/072965, filed on Sep. 13, 2017, which claims priority to German Patent App. No. DE 10-2016-118-123.4, filed on Sep. 26, 2016, the disclosures of which are incorporated by reference in their entirety.

FIELD OF THE INVENTION

The invention relates to a holding device, particularly a holding arm and/or stand, for medical purposes, particularly for holding surgical mechatronic assistance systems and/or surgical instruments. The invention further relates to a method.

BACKGROUND

Holding arms falling under the type of holding devices indicated above have long been known and are used in surgery particularly for relieving a user of static effort. Such a holding arm is used in order to mount a mechatronic assistance system and/or a surgical instrument such as a manipulator, an endoscope, a surgical clamp, and the like. Holding arms of the above type have proven themselves particularly for holding endoscopes. For endoscopic surgery, a user typically operates an instrument with both hands while an assistant holds the endoscope in order to make the operating field visible on a screen. Holding the endoscope over a longer period of time is very fatiguing. For this reason, the above mentioned holding arms are increasingly used.

One such holding arm, for example, is known from DE 195 26 915 B4. The holding device for medical purposes disclosed there comprises a connecting part and a mount for surgical tools and an arm disposed between the mount and the connecting part. The arm is connected to the mount and the connecting part, or to an adjacent arm, via a joint and overcoupled to a pneumatically actuated device for selectively fixing and releasing the joints, wherein said device fixes the joints by the effect of a mechanical spring applying a braking force to the joint, and wherein the device can be pneumatically transitioned into a state releasing the joint against the force of said spring. An actuating member is disposed at the proximal end of the arm, by means of which a valve can be opened so that the individual joints of the arm can be adjusted. When the actuating member is released, the valve is closed again, so that the joints are fixed. A disadvantage is that all joints are opened simultaneously by means of the holding arm, whereby positioning can be difficulty.

A similar holding arm is disclosed in EP 1 958 587 B1. The holding arm disclosed there also comprises a plurality of joints and a touch-sensitive sensor is provided for actuating the joints. The sensor is disposed on the holding arm adjacent to the medical instrument, so that when gripping the medical instrument, the operator makes contact with the touch-sensitive sensor, whereby all joints of the holding arm are released. Here again the above problem of insufficient positioning occurs.

The problem that the operator is unclear about whether all joints are actually released, how far said joints are opened, and what motions are permissible persists for both of the above holding arms.

Robotic systems are further increasingly used in surgery and are mounted on such a holding arm, for example. In modern surgical environments, surgical navigation systems using electromagnetic radiation are used, particularly infrared radiation or an electromagnetic field. It can be advantageous if the robotic system is registered to the navigation system. To this end, the robotic system must be "visible" to the navigation system. Infrared reflectors having a particular geometry and known as trackers are typically used to this end. The trackers are attached to all objects to be navigated, such as instruments, devices, and target region (patient). The surgical navigation system can then detect by means of a camera the position of the instruments relative to the patient or a CT data set using the reflection of IR radiation. The trackers typically have three reflection points and the position and orientation of the tracker in space, within the coordinate system of the camera, can be determined by means of triangulation using the two cameras.

SUMMARY OF THE INVENTION

The object of the present invention is to further improve safety in surgery with respect to holding arms and to simplify the use thereof.

The object is achieved according to the invention by a holding device having the features of claim 1, particularly a holding device for medical purposes for holding an attached device, having a proximal end for attaching the holding device to a base and a distal end for receiving an attached device; at least one first and one second arm segment, the first arm segment being connected to a first joint and the second arm segment being connected to a second joint, each joint being releasable and lockable; an operator control device for releasing and/or locking the corresponding joint for placing the holding device in a desired pose; and a control unit comprising hardware and program code means for controlling the holding device, wherein the holding device further comprises at least one receiver for electromagnetic radiation connected to the control unit and adapted for transmitting signals to the control unit on the basis of electromagnetic signals received from a surgical navigation system. The holding device can preferably be operated in a navigation mode and in an operator mode, wherein the holding device can be operated purely manually in the operator mode by means of an operator control unit provided for the holding device, and is prepared for receiving commands from the navigation system in the navigation mode, wherein the control unit is set up for determining on the basis of the received signal that the holding device is present in a navigated surgical environment and for switching to the navigation mode.

The invention is based on the insight that the holding device can be integrated in an existing surgical navigation environment particularly easily and usefully by means of such a receiver. Surgical navigation systems typically use infrared or electromagnetic radiation for identifying individual objects present in the operating area. The holding device receives the electromagnetic radiation by means of the receiver and transmits a signal to the control unit. The control unit determines, preferably on the basis of the received signal, that the holding device is present in a navigated surgical environment. This means that when the electromagnetic radiation is received, the holding device autonomously recognizes that said device is present in a field of vision of the surgical navigation system or the camera of such a system, without requiring an additional external signal to this end, such as a user entry or status signal from the surgical navigation system transmitted by wire or wirelessly. The holding device is thus able to autonomously detect when said device is present in the field of vision of the surgical navigation system.

The holding device preferably comprises at least one navigation mode and one operator mode, wherein the holding device can be operated purely manually in the operator mode, that is, by manual contact, by means of an operator control unit such as a special laptop provided for the holding device, a remote control or the like, or by means of a connected computer. In the navigation mode, the holding device is preferably coupled to the navigation system and prepared for receiving commands from the navigation system. If the control unit determines that the holding device is present in a navigated surgical environment, then the control unit preferably switches into navigation mode. In navigation mode, it can be provided that various functions of the holding device are modified, such as the maximum angle at the joints and/or the enabling or locking of the corresponding joints. For example, it can be provided that the operator control device is locked in this case, and that manually operating the holding device is not permitted.

The holding device, however, need not necessarily be controlled by the navigation system. The invention is based on the idea that the holding device autonomously detects that said device is present in a navigated environment. No change to an existing surgical navigation system is required therefor. The surgical navigation system is also not required to be particularly implemented or prepared for operating in conjunction with the holding device according to the present invention. Solely on the basis of the receiving of the electromagnetic radiation of the surgical navigation system, the holding device detects that said device is in the field of view thereof. In this case, the receiver sends a corresponding signal to the control unit. The receiver is a wireless receiver.

The holding device further internally comprises a BUS system and a first mechatronic interface at the proximal end and a second mechatronic interface at the distal end. The holding device can preferably be connected for data transfer to the interface at the proximal end, and to further systems, such as a CAM system or a surgery documentation device. The holding device preferably comprises an attached device at the distal end thereof, particularly a robotic attached device. A robotic attached device particularly comprises a manipulator a having one or more actuators, particularly servomotors, and is provided for displacing and guiding a surgical instrument such as an endoscope or the like.

The holding device is preferably set up for receiving via the receiver actuating signals fed through the control unit and the internal BUS system, preferably via the interface at the distal end, to a received attached device, particularly a robotic attached device. In this manner, it is possible for the holding device to receive actuating signals for the robot attached device via the navigation system wirelessly, namely via the electromagnetic radiation. Integrating the holding device in a navigated surgical environment is thereby particularly simple.

The receiver preferably comprises an infrared sensor. Such an infrared sensor is preferably implemented as an infrared diode. The receiver preferably comprises a plurality of infrared sensors. One infrared sensor is preferably provided at least at each arm segment and/or at each joint. Preferably, 2, 3, or 4 infrared sensors are disposed about the circumference of each arm segment. It is thereby possible that the infrared signal of the surgical navigation system is received regardless of the pose of the holding device. In one variant, a plurality of infrared sensors are provided about the circumference on only one arm segment, for example the middle or distal arm segment. If the infrared sensors serve only for receiving signals and forwarding signals to a central control unit of the holding device, then it is sufficient that such infrared sensors are provided on only one arm segment for central communication. Alternatively, it is also conceivable that the receiver comprises one or more CCD chips.

In a preferred refinement, the receiver comprises a Hall-effect sensor. Instead of a Hall-effect sensor, another suitable sensor adapted for detecting an electromagnetic field can be provided. By means of Hall-effect sensors, it is possible to capture the strength of an electromagnetic field, and thus to communicate signals from a navigation system working with electromagnetic (EM) fields and comprising an EM field generator. The Hall-effect sensor transmits a corresponding signal when receiving the electromagnetic field, so that the corresponding arm segment on which the Hall-effect sensor is provided detects when the corresponding segment is present in the working volume of the EM field generator.

According to a further preferred embodiment, the receiver comprises a 3D magnetometer. A 3D magnetometer is preferably disposed in at least two arm segments, preferably in all arm segments of the holding device. By means of such 3D magnetometers, it is possible to determine the position of the corresponding arm segment in which the magnetometer is disposed in the electromagnetic field of the EM generator. On the basis of data received by the control unit from the 3D magnetometers, the pose of the holding device can be determined. Said pose, determined by the holding arm itself, can be provided by means of the control unit and via the internal BUS system to the interface at the proximal end and forwarded to the surgical navigation system via a wired or wireless connection. On the basis thereof, a comparison can be performed between a pose determined by the surgical navigation system by means of a detecting device thereof and the pose determined by the holding device itself. Calculation errors can thereby be compensated for, in that the two poses are compared. Safety is thereby further improved.

According to a further preferred embodiment of the invention, the holding device comprises at least one transmitter for transmitting electromagnetic radiation for transmitting signals to a surgical navigation system. Such a transmitter for transmitting electromagnetic radiation preferably comprises an active transmitter. It is also preferable that said transmitter comprises a passive transmitter. A passive transmitter is understood here particularly as a reflector reflecting electromagnetic radiation emitted by the surgical navigation system. An active transmitter is understood as a transmitter emitting itself, such as an IR LED.

By means of such a sensor, it is possible that the holding device not only receives signals from surgical navigation systems, but also transmits signals to the surgical navigation system. Such signals particularly comprise the position of one or more arm segments of the holding device and a status of the holding device. It is preferable, for example, that one or more active sensors are implemented for emitting a signal when the holding device changes to a particular status. For example, the one or more active transmitters are implemented for outputting a signal when one or more brakes at the joints are opened and/or one or more joints are displaced. It is also possible that the one or more active transmitters transmit the self-determined pose of the holding device by means of electromagnetic signals. Wireless data transmission between the holding device and the surgical navigation system is thereby achieved without using any additional devices, such as WLAN or the like. Rather, the transmitting process immanent to the navigation system is used, namely particularly infrared radiation or electromagnetic radiation.

The transmitter preferably comprises at least one infrared light source. The infrared light source is preferably implemented as an infrared LED. A plurality, that is, at least two, of said infrared light sources are preferably provided.

The holding device particularly preferably comprises a first display unit disposed on the first joint and a second display unit disposed on the second joint, wherein the first and/or second display unit each comprise at least one IR light source and are set up for displaying at least one status of the holding device and/or a status of an attached device. The display units preferably comprise light sources emitting light in the visible range, particularly such as LEDs, in addition to IR light sources. It is further preferable that the display units comprise IR photodiodes for receiving infrared radiation, wherein the IR photodiodes are part of the receiver.

The display units are preferably annular and disposed coaxial to the axes of rotation of the joints. The specific design of the display units is described in PCT/EP2016/069167, the disclosed content thereof being incorporated here by reference. Reference is made expressly to the disclosure in PCT/EP2016/069167 for the design of the display units. The display units also indicate the status of the holding device visually for the perception of a user. A user can thereby directly recognize which signals and what information the holding device is transmitting to the surgical navigation system.

According to a further preferred embodiment, the one or more active transmitters are implemented for outputting a signal when one or more brakes at the joints are opened and/or one or more joints are displaced. The holding device preferably comprises brakes at the joints for opening by means of an operator control device. When said brakes are opened, the holding device can be displaced, that is, the pose thereof can be changed. The one or more active transmitters preferably emits a signal in this case. It can also be provided that a signal is emitted only if one or more joints is displaced. Merely opening the brake does not yet change the pose of the holding device. Rather, it is essential that one of the joints be displaced. It is therefore preferable that in this case a signal is emitted. In this manner, it is possible that the holding device informs the surgical navigation system of an imminent displacement or a displacement actually occurring. The signal preferably represents the one or more released joints. The signal preferably represents the one or more displacements of the one or more joints, preferably the speed and/or acceleration. The signal preferably represents the pose assumed by the holding device after completing the displacement and/or setting the one or more brakes.

According to a further preferred embodiment, the holding device comprises a navigation camera for capturing an operating field. The holding device is preferably set up for providing signals captured by the navigation camera to an interface for the surgical navigation system. The interface can be a physical interface at the proximal end of the holding device, so that the signals are provided to the surgical navigation system via a cable. The signals captured by the navigation camera are preferably provided to a surgical navigation system wirelessly via a transmitter for transmitting electromagnetic radiation for transmitting signals. In this manner, it is possible that the holding device itself observes the operating field by means of the integrated navigation camera thereof. It can be that the holding device obscures the operating field or a part thereof relative to the surgical navigation system and the camera of the surgical navigation system. If the holding device itself comprises a navigation camera, then an image of the obscured region can also be made and provided to the surgical navigation system. The surgical navigation system can then merge the signals from the navigation camera associated with the surgical navigation system and the navigation camera on the holding arm, in order to thus obtain an overall image of the operating field without obscuring by the holding device.

The data captured by the navigation camera can be provided in processed or unprocessed form. For unprocessed provision of the data, said data is simply captured by the navigation camera and then provided to the holding device at a corresponding interface. The processed data can further comprise data about the pose of the holding device and a location of the navigation camera and viewing direction of the navigation camera of the holding device, in addition to the location data. It is also conceivable that processed data comprises additional information about objects present in the operating field and captured by the navigation camera on the holding device.

It is further preferable that the holding device comprises a bus system and a first mechatronic interface at the proximal end and a second mechatronic interface at the distal end, wherein the mechatronic interface at the distal end is provided for coupling to a robotic attached device. The data of the navigation camera can also be transferred by means of the first mechatronic interface at the proximal end.

According to a second consideration of the invention, the above object is achieved by a robotic attached device, particularly a manipulator device, having a frame, a drive supported on the frame, an instrument receptacle for holding a surgical instrument for driving by means of the drive, and a mechatronic interface for coupling to a distal interface of a holding device, particularly a holding device according to any one of the preferred embodiments of a holding device described above according to the first consideration of the invention, wherein at least one receiver for electromagnetic radiation is provided and is connate to a robot control unit and adapted for transmitting signals to the robot control unit on the basis of received electromagnetic signals of a surgical navigation system. The robotic attached device is provided for coupling to a holding device. The object is thus also achieved in that the robotic attached device itself determined that said device is present in a navigated environment, as has already been fundamentally described with respect to the holding device according to the first consideration of the invention. It should thus be understood that the holding device according to the first consideration of the invention and the robotic device according to the second consideration of the invention comprise identical and similar subconsiderations, as particularly stipulated in the dependent claims. In this respect, reference is made to the receiver of the holding device and the control unit of the holding device according to the first aspect of the invention for preferred embodiments and advantages of the receiver and the robot control unit.

The robot control unit preferably interacts with the control unit of the holding device via the mechatronic interface and exchanges data with the same, particularly signals received by the receiver of the robotic attached device or the receiver of the holding device.

The robotic attached device can preferably be operated in a robot navigation mode and in a robot operator mode, wherein the attached device can be operated purely manually in the robot operator mode by means of a robot control unit provided for the attached device, and in the robot navigation mode is prepared for receiving commands from the navigation systems, wherein the robot control unit is set up for determining on the basis of the received signal that the attached device is present in a navigated surgical environments and for switching into the robot navigation mode. The robotic attached device is preferably set up for providing a navigation signal to the mechatronic interface in response to a signal received by the receiver. By means of the mechatronic interface, the navigation signal can then be transferred to the holding device, said holding device processing the signal further or providing the signal directly to the holding device at the proximal interface. Such a navigation signal can be used for indicating that the robotic attached device is in the robot navigation mode. Such a signal can also be used for automatically creating a surgical report. According to a further preferred embodiment, the robotic attached device comprises a first mount and second mount for holding an instrument receptacle for the surgical instrument, a first suspension arm arrangement support on the frame and connecting the frame to the first mount in an articulated manner, and a second suspension arm arrangement connecting the frame to the second mount in an articulated manner, wherein the first and second suspension arm arrangements are each displaceable in first and second motion planes parallel to each other and spaced apart, so that the first mount is displaceable in the first motion plane and the second mount displaceable in the second motion plane, wherein the first suspension arm arrangement is coupled to the frame at four lever pivot points of the first suspension arm arrangement, and the second suspension arm arrangement is coupled to the frame at four lever pivot points of the second suspension arm arrangement.

The result is a robotic attached device for displacing the first and second mounts in separate motion planes always disposed parallel to each other. Pivoting of the planes relative to each other is not implemented. A joint in the frame can thereby be eliminated and the frame can be more rigid overall. Each suspension arm arrangement is further coupled to the frame by means of four lever pivot points, whereby greater rigidity is achieved in turn. For purely positioning the first and second mount, two lever pivot points per suspension arm arrangement are fundamentally sufficient. The two further points preferably provided in each case then particularly serve for stabilizing.

The four first lever pivot points and the four second lever pivot points are preferably disposed in a V shape in each case. The suspension arm arrangements are thus prevented from assuming singularities. Due to the V-shaped arrangement of the four lever pivot points of each suspension arm arrangement, each position of the first and second mount is unique. Geometrically or statically indeterminate positions are avoided. The safety of the surgical manipulator device is thereby particularly substantially increased, because singularities cannot occur in the kinematics during an operation. An arrangement of the four first lever pivot points and the four second lever pivot points in a rectangle in each case is indeed preferred as part of the invention, but then other means should be provided for preventing singularities, such as a limit on freedom of motion.

According to a third consideration of the invention or a preferred refinement of the second consideration of the invention, the robotic attached device comprises a frame, a drive supported on the frame, an instrument receptacle for holding a surgical instrument and driven by the drive, and a mechatronic interface for coupling to a distal interface of a holding device, particularly a holding device according to any one of the preferred embodiments of a holding device according to the first consideration of the invention as described above, and a navigation camera for capturing an operating field.

The robotic attached device preferably set up to this end for providing signals captured by the navigation camera to an interface for the surgical navigation system and/or to the mechatronic interface in a processed or unprocessed form.

According to the present third consideration of the invention, the robotic attached device comprises the navigation, and not the holding arm. Nevertheless, it should be understood that the robotic attached device according to the third consideration of the invention and the holding arm according to the first consideration of the invention comprise identical and similar subconsiderations, as far as the navigation camera is concerned, as particularly stipulated in the dependent claims. In this respect, reference is made in full to the above description of the first consideration of the invention of the holding device having the navigation camera disposed thereon.

By providing the navigation camera on the robotic attached device, the operating field can be observed even better. No further obscuring occurs by elements of the robotic attached device relative to the navigation camera of the holding arm. The robotic attached device can also be robotically controlled, while the holding arm is preferably passive overall. That is, it is conceivable that commands, such as signals wirelessly transferred by means of electromagnetic radiation from the surgical navigation system to the holding device and/or to the robotic attached device are adapted, modified, or otherwise controlled to a direction of view of the navigation camera on the robotic attached device. It can also be provided that the navigation camera on the robotic attached device comprises a voice control system, such that commands spoken by an operator are converted into electrical signals for controlling the navigation camera. It is conceivable, for example, that an operator speaks the word "snapshot" and the navigation camera takes a photo, said photo then being transferred via the robotic attached device and the mechatronic interface of the robotic attached device to the mechatronic interface at the distal end of the holding device, and from there via the internal bus system to the proximal interface of the holding device and made available there.

The robotic attached device according to the second and/or third consideration of the invention preferably comprises at least one transmitter for transmitting electromagnetic radiation for transmitting signals to a surgical navigation system. Such a transmitter for transmitting electromagnetic radiation for transmitting signals to a surgical navigation system has also been described above with respect to the holding device. Nevertheless, it is also preferable that the robotic attached device comprises such a transmitter. The robotic attached device is robotically controlled, that is, said device autonomously modifies the pose thereof on the basis of received electronic signals.

According to a fourth consideration of the invention, the object indicated above is achieved by a system comprising a holding device according to any one of the preferred embodiments of a holding device according to a first consideration of the invention, and comprising an attached device received at the distal end thereof, wherein the attached device comprises at least one transmitter for transmitting electromagnetic radiation for transmitting signals to a surgical navigation system. The attached device is preferably a robotic manipulator. The transmitter of the attached device is preferably constructed for corresponding to the transmitter of the holding device and preferably comprises one or more IR light sources.

According to a fifth consideration, the object stated above is achieved by a system comprising a holding device according to any one of the preferred embodiments of a holding device according to the first consideration described above and an attached device received at the distal end of the holding device, wherein the attached device comprises at least one receiver for electromagnetic radiation.

The attached device preferably comprises an interface by means of which the attached device can be coupled to the internal BUS system of the holding device. Both the transmitter and the receiver of the attached device according to the systems of the second and third considerations of the invention are preferably coupled to the control unit of the holding device via the BUS system. It is further preferable that the attached device comprises a dedicated control unit. Both the transmitter and the receiver are correspondingly coupled to the control unit of the attached device and/or to the control unit of the holding device via the BUS system. For the present embodiment, wherein the attached device comprises a receiver, it is possible that the surgical navigation system transmits signals and particularly commands to the attached device by means of the type of radiation, electromagnetic field, or infrared radiation used by the surgical navigation system. The attached device can correspondingly transmit signals, particularly the status thereof, to the surgical navigation system.

According to a sixth consideration of the invention, the object stated above is achieved by a method for communicating between a holding device according to any one of the preferred embodiments described above of a holding device according to a first consideration of the invention and a surgical navigation system, having the steps: Receiving electromagnetic radiation from a surgical navigation system by means of the receiver; transmitting a corresponding signal from the receiver to the control unit; processing the signal received by the receiver by means of the control unit; and switching the holding device into a navigation mode. The step of processing preferably comprises detecting by means of the control unit that the holding device is present in a navigation region of the surgical navigation system. The holding device preferably comprises at least one navigation mode and one operator mode, wherein the holding device can be operated purely manually in the operator mode, that is, by manual contact, by means of an operator control unit such as a special laptop provided for the holding device, a remote control or the like, or by means of a connected computer. In the navigation mode, the holding device is preferably coupled to the navigation system and prepared for receiving commands from the navigation system. If the control unit determines that the holding device is present in a navigated surgical environment, then the control unit preferably switches into navigation mode. Alternatively, a navigation system can also specify that the holding device is present in a navigated environment. For example, the navigation system transmits a corresponding signal via the proximal interface of the holding device to said device in order to cause the holding device to switch to the navigation mode. Autonomous determining by the holding device is then unnecessary. In navigation mode, it can be provided that various functions of the holding device are modified, such as the maximum angle at the joints and/or the enabling or locking of the corresponding joints. For example, it can be provided that the operator control device is locked in this case, and that manually operating the holding device is not permitted. In the navigation mode, it is preferably provided that signals transmitted by the receiver to the control unit are processed and provided for transfer to the navigation system at the proximal interface. The receiver can comprise one or more IR sensors, one or more Hall-effect sensors, and/or one or more 3D magnetometers, wherein the list is not exclusive.

The method further comprises the steps: transmitting commands of the surgical navigation system to the holding device by means of the electromagnetic radiation; and receiving the commands by means of the receiver. The receiver receives the signals and transmits the same to the control unit, processes the signals in the processor using the program code means, and causes one or more actuators of the holding device to perform one or more operations. In addition or alternatively, the control unit transmits corresponding signals to an attached device received at the distal interface, causing one or more actuators of the attached device to perform one or more operations.

In a further preferred embodiment of the method, the holding device comprises at least one transmitter for transmitting electromagnetic radiation for transmitting signals to a surgical navigation system and the method comprises the steps: transmitting electromagnetic radiation for transmitting signals to the surgical navigation system by means of the transmitter, and receiving the signals at the surgical navigation system, wherein the signals represent a status of the holding device and/or of an attached device. It is thereby possible that the holding device provides the status thereof to the surgical navigation system by means of the transmitter. The transmitter preferably comprises one or more infrared light sources. The method preferably comprises emitting infrared radiation at a particular frequency, or at a predetermined pulse schema, for transmitting information to the surgical navigation system. Transmitting information by means of a predetermined pulse schema can be understood as analogous to Morse code. It is conceivable, for example, that the IR light source blinks according to a predefined schema in order to provide the current pose of the holding device to the surgical navigation system. Other information, such as a readiness status, opening of joints, the type of attached device, and the like can also be provided.

In a particularly preferred embodiment of the method, wherein the holding device comprises at least one 3D magnetometer and the holding device is disposed in an electromagnetic field of a surgical navigation system, the method comprises the steps: determining a relative pose of the holding device relative to the electromagnetic field on the basis of the at least one 3D magnetometer; determining an absolute pose of the holding device; comparing the relative and absolute pose of the holding device; and determining an error of the electromagnetic field by means of an error correcting unit on the basis of the comparison of the relative and absolute pose of the holding device. Surgical navigation systems based on electromagnetic fields, generated by EM field generators, have the inherent problem that objects brought into the navigation region, particularly such as instruments or the like, influence the electromagnetic field and therefore determining the position of said objects in the electromagnetic field can have an error. The electromagnetic field actually prevalent in the navigation region deviates from that generated by the EM field generator. A holding device of the type described above comprises a plurality of components able to influence the electromagnetic field, particularly such as electromagnetic brakes in the joints. The influence of such a holding device on an electromagnetic field is therefore comparably high. On the basis of the one or more 3D magnetometers, the pose of the holding device relative to the electromagnetic field prevalent in the navigation region can be determined according to the present embodiment. Determining the relative pose of the holding device can be performed by the holding device itself, that is, by the control unit. In one variant, the signals of the 3D magnetometer processed by the control unit are transmitted by wire or wirelessly to a unit external to the holding arm, such as the surgical navigation system, and said unit determines the relative pose.

Comparing the relative and absolute poses of the holding device can also be performed either by the control unit of the holding device or by a unit external to the holding device. Based on the comparison, an error of an electromagnetic field is determined by means of an error correcting unit. The error correcting unit can be a unit of the control unit of the holding device, or a unit external to the holding device, for example in the surgical navigation system.

In a preferred refinement, said determined error is used for determining a position of an object present in the electromagnetic field. The surgical navigation system determines the position of one or more objects present in the electromagnetic field, particularly such as surgical instruments and the like. Because the electromagnetic field prevalent in the navigation region is not identical to that generated by the EM field generator, because said field has been modified by the holding device, for example, it can occur that the position determined by the surgical navigation system with respect to the object is not correct. Because the error of the electromagnetic field is known, however, it is possible to correct the positions determined with respect to the object. The accuracy of determining the position of objects in the navigation region is thereby improved.

In a preferred refinement, the step comprises determining the absolute pose of the holding device, determining settings of the joints of the holding device, and calculating the absolute pose based on the settings of the joints. To this end, position sensors are preferably provided in the joints and connected to the control unit via the internal BUS system. By capturing the settings of the individual joints, particularly the rotary positions thereof, the pose of the holding device can be calculated. The pose calculated by the control unit or an external unit is preferably provided at the proximal interface and transmitted to the error correcting unit.

Alternatively or additionally, the absolute pose of the holding device is determined by optically capturing the absolute pose of the holding device by means of an optical capture unit. Optically capturing is based particularly on IR reflection. The surgical navigation system can additionally comprise IR cameras and IR transmitters for emitting IR radiation. IR reflectors can be provided on the holding device so that the surgical navigation system can optically determine the absolute pose of the holding device on the basis of the transmitted IR radiation and the reflection. In addition, the holding device can itself comprise active IR transmitters, wherein the surgical navigation system is provided for optically determining the absolute pose of the holding device on the basis of the signals transmitted by the active IR transmitters. The designation of the absolute pose refers here to a pose independent of the electromagnetic field, and the term absolute pose particularly also comprises a pose determined relative to a surgical table or to the surgical navigation system. Because the positions of the surgical table and of the surgical navigation system are known, such a pose is also designated as an absolute pose.

According to a seventh consideration of the invention, a method is proposed for communicating between a holding device or a holding device having an attached robotic device disposed thereon and a surgical navigation system, having the steps: capturing a region obscured by the holding device for the surgical navigation system by means of a navigation camera disposed on the holding device; providing optical data captured by the navigation camera to the surgical navigation system. The navigation camera can, as proposed in the first consideration of the invention, be disposed directly on the holding device, or as proposed in the third consideration of the invention, disposed indirectly on the holding device, namely directly on the robotic attached device, said device being in turn attached to the holding device.

The method preferably comprises the step: merging optical data captured by the surgical navigation system and the optical data captured by the navigation camera for retaining an image without a region obscured by the holding device.

According to an eighth consideration of the invention, the object state above is achieved by a computer program having program code means causing a processor to execute the steps of the method for generating a code according to any one of the embodiments according to the fourth consideration of the invention described above when said program code means are executed by the processor.

BRIEF DESCRIPTION OF THE DRAWINGS

The invention is described in more detail below with reference to the attached figures. Shown are.

DETAILED DESCRIPTION

Figure 4:
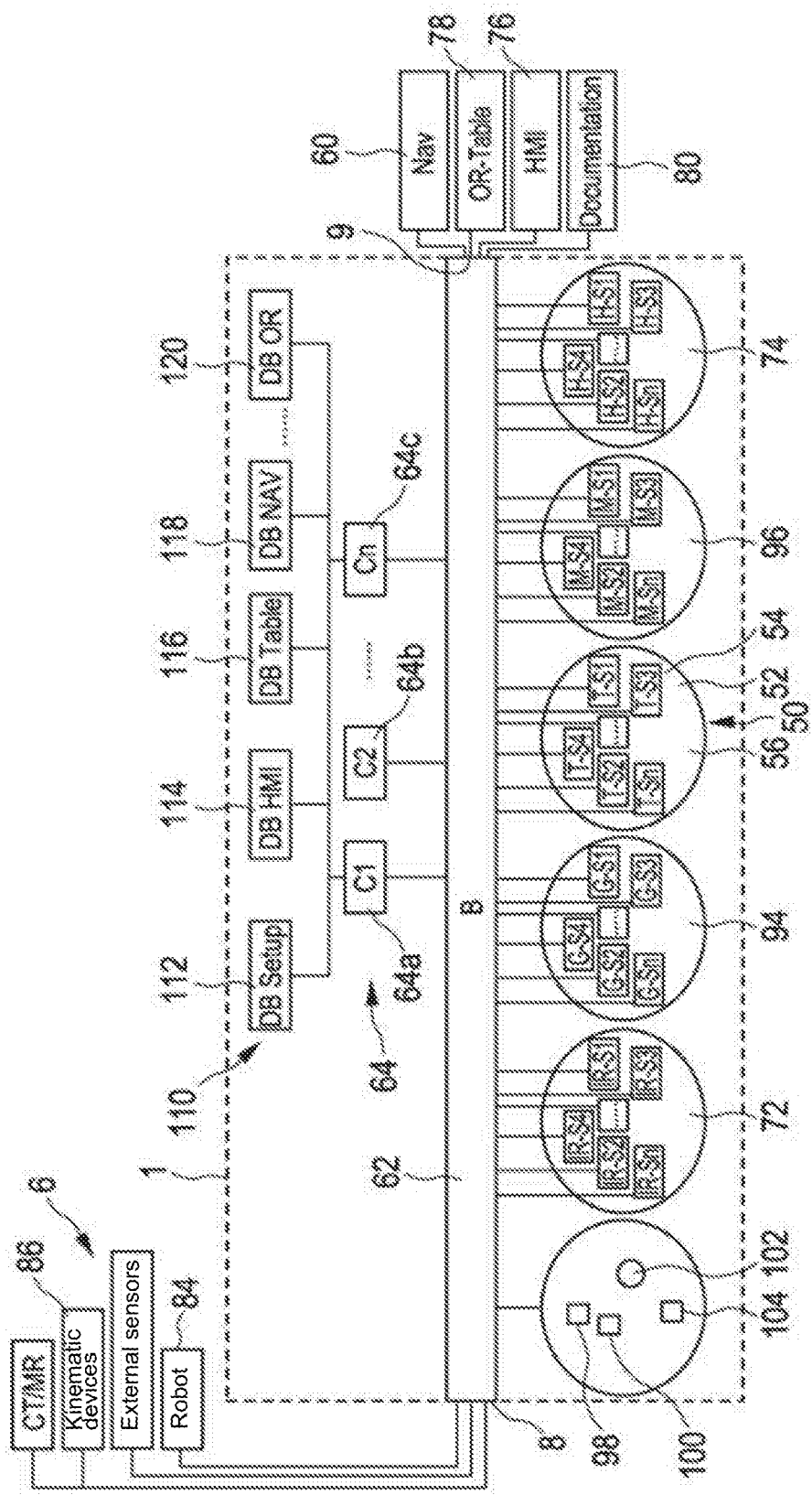
FIG. 4 A schematic diagram for constructing the holding device according to a further embodiment example, FIG. 5 A further diagram of construction of a holding device according to the invention, FIG. 6 A perspective representation of the holding device according to the invention, FIGS. 7a-7c A schematic representation of a display unit in three different states, FIGS. 8a-8c A further schematic representation of a display unit in three different states, FIG. 9 A perspective representation of a holding device having a robotic attached device mounted thereon in a further embodiment example, FIG. 10 A magnified view of the robotic attached device according to FIG. 9, FIG. 11 A further perspective representation of the holding device, including the robotic attached device from FIG. 9, with a surgical instrument, and FIG. 12 A perspective representation of a holding device according to a further embodiment example.
Figure 5:
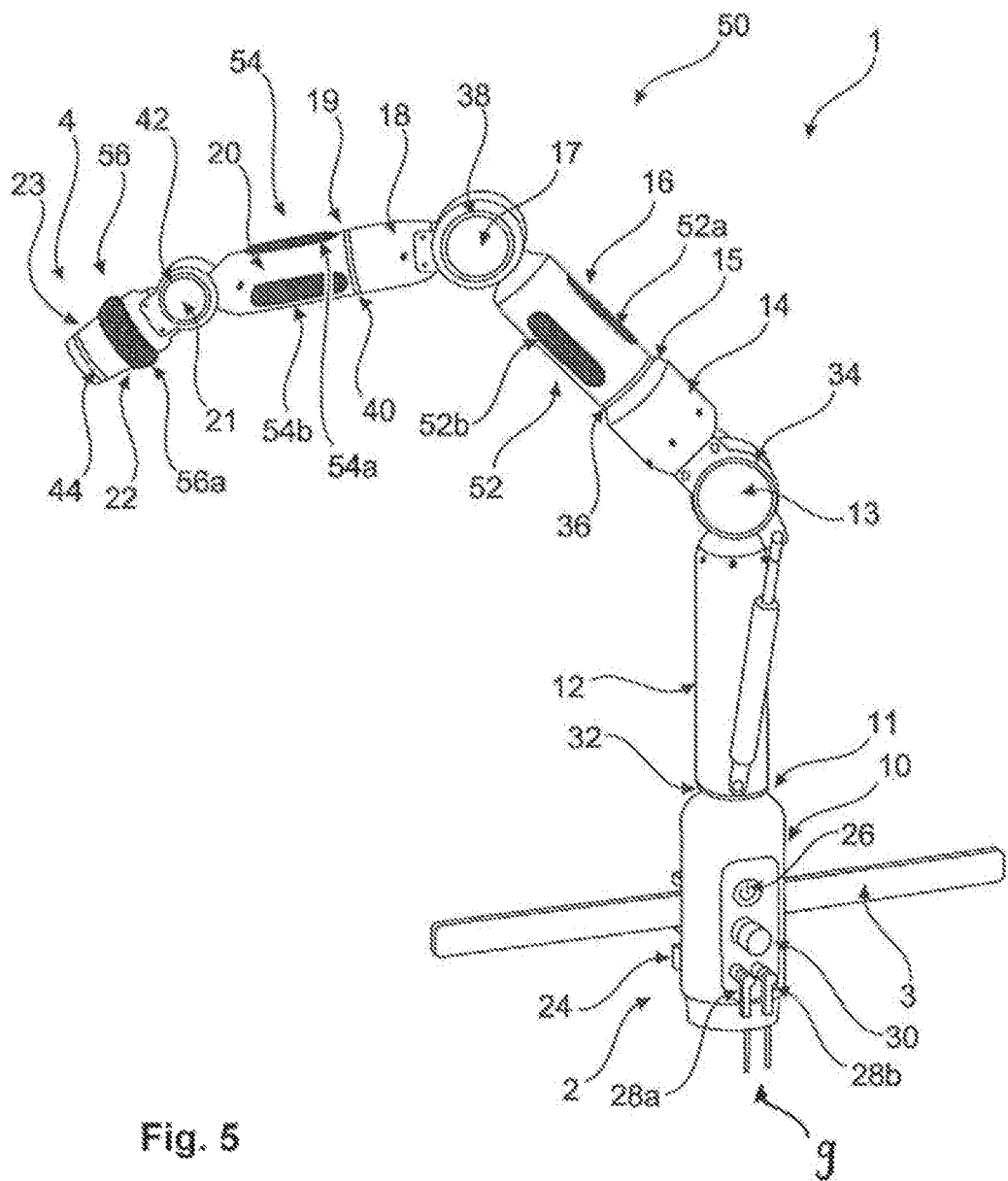

A holding device 1 (FIG. 1) has the form of a holding arm and comprises a proximal end 2 for attaching the holding device 1 to a base (cf. FIG. 5). The holding device 1 further comprises a distal end 4 for receiving an attached device 6 (cf. FIGS. 3-6). An interface 8 is provided at the distal end 4, serving for coupling to the attached device and for transferring data and electrical power to and from the same. A second interface 9 is provided at the proximal end 2 and serves for connecting the holding device 1 to a surgical navigation system 60 (cf. particularly FIGS. 3 and 4).

Altogether the holding device 1 according to the present embodiment example comprises seven arm segments 10, 12, 14, 16, 18, 20, 22, wherein the joints 11, 13, 15, 17, 19, 21, 23 are provided between the individual arm segments 10 through 22. The joints 11, 15, 19, and 23 are implemented as rotary joints and the joints 13, 17, and 21 as pivot joints. That is, the axes of rotation of the joints 11, 15, 19, and 23 lie substantially within the plane of the drawing relative to FIG. 1, while the axes of rotation of the joints 13, 17, and 21 extend substantially perpendicular to the plane of the drawing.

The holding device 1 further comprises a BUS system 62 extending from the proximal interface 9 to the distal interface 8 and coupled there to the corresponding interfaces 8, 9. The holding device 1 further comprises one processor unit 64a, 64b in each arm segment (only two shown in FIG. 3) also connected to the BUS system 62. Each of the processor units 64a, 64b provided in each arm segment (thus seven altogether in the embodiment example from FIG. 1) serve to control individual brakes at the joints 11 through 23. Altogether, the processor units 64a, 64b together form a control unit 64 of the holding device 1, altogether controlling functions of the holding device 1.

Figure 1:
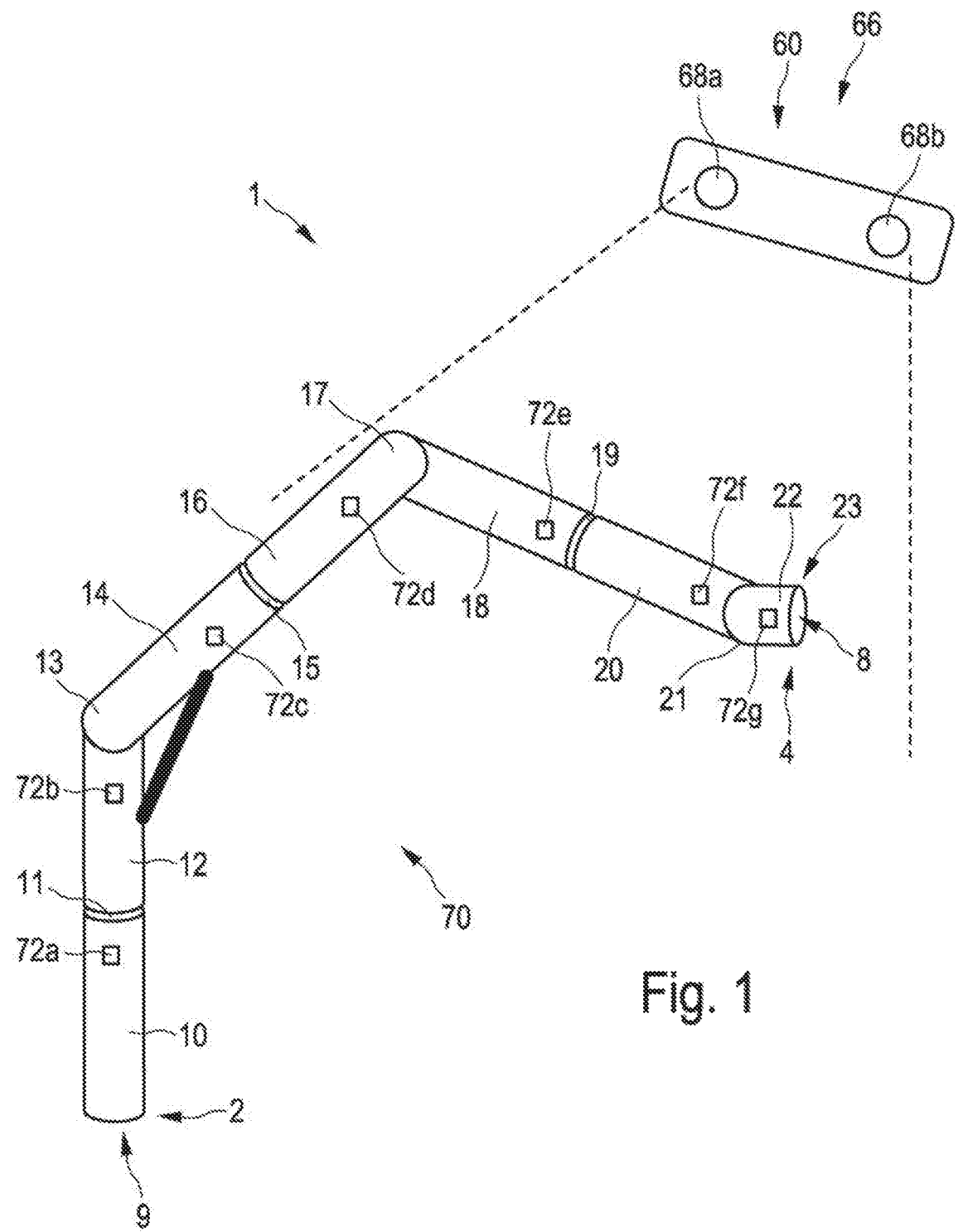
FIG. 1 A side view of a holding device according to the invention.

According to the invention, the holding device 1 comprises a receiver 70 provided for receiving electromagnetic radiation of the surgical navigation system and connected to the control unit 64 and adapted for transmitting signals to the control unit 64 on the basis of the received signals of the surgical navigation system 60. The receiver 70 according to the embodiment example shown in FIG. 1 comprises a plurality of infrared sensors, namely IR photodiodes 72a, 72b, 72c, 72d, 72e, 72f, 72g (altogether labeled as 72; cf. FIG. 3). In FIG. 1, one IR photodiode 72 is disposed on each arm segment 10 through 22. It is preferable, however, that two, three, four, or more IR photodiodes are disposed about the circumference of each arm segment 10 through 22, so that at least one IR photodiode 72 is always aligned so as to be able to receive IR radiation from the surgical navigation system 60 regardless of the pose of the holding device 1. The surgical navigation system 60 according to the present embodiment example (FIG. 1) is implemented as an optical surgical navigation system 66 comprising two infrared cameras 68a, 68b. The surgical navigation system 66 transmits infrared radiation, for example in the form of IR flashes or pulses and can thereby transfer commands or other information and data to the holding device 1. The holding device 1 is further implemented for detected that the device is present in a navigated environment when receiving infrared radiation from the surgical navigation system 66 by means of the IR photodiodes. The control unit 64 is then implemented for switching the holding device into a navigation mode in which individual functions of the holding device 1 are modified, particularly locked out.

Figure 2:
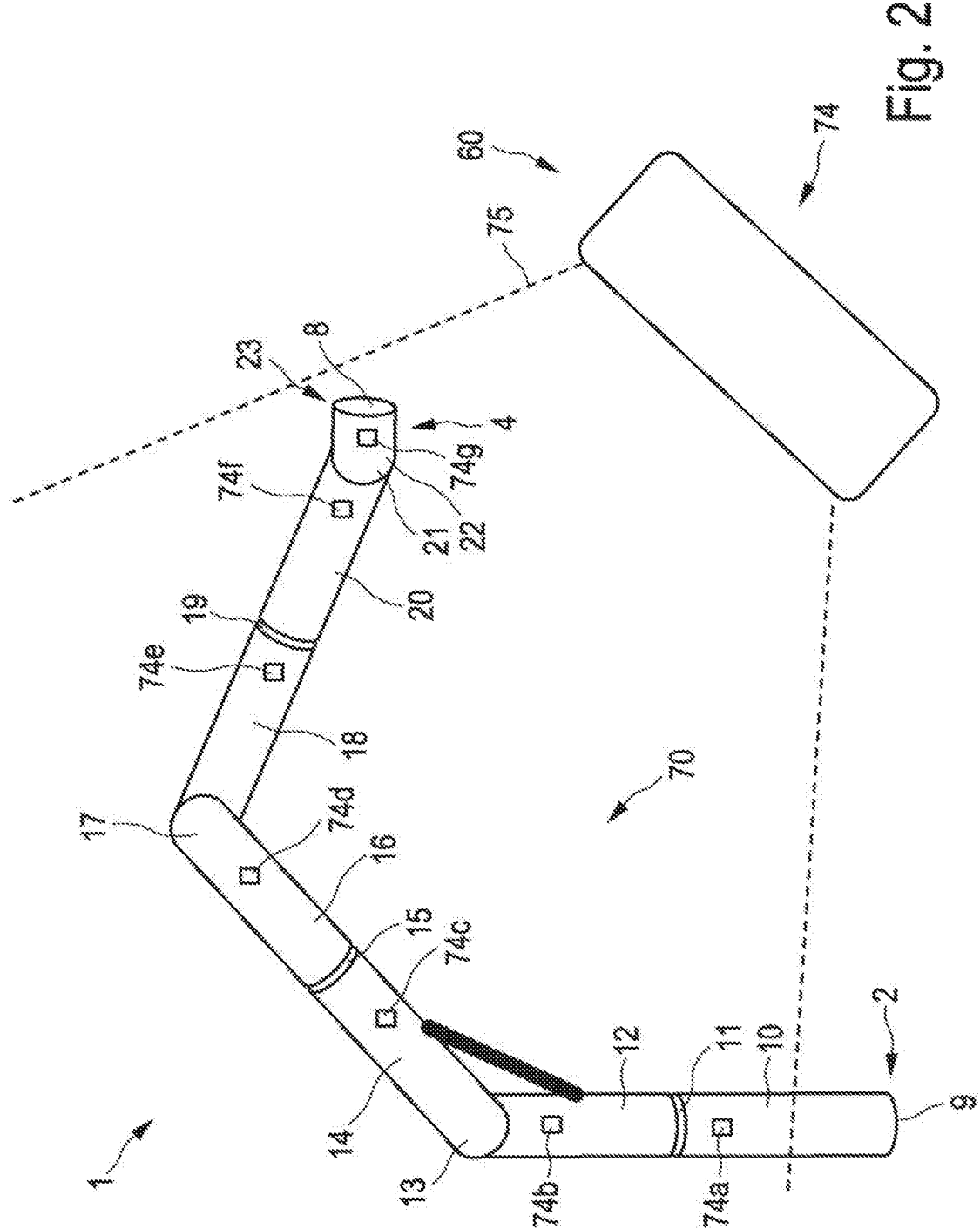
FIG. 2 A further embodiment of the holding device according to the invention.

FIG. 2 shows a variant of the embodiment according to FIG. 1. Fundamentally, FIG. 2 also shows a holding device 1 substantially identical to the holding device according to FIG. 1. Identical and similar elements are labeled with identical reference numerals, so that full reference is made to the description of FIG. 1 above. In the embodiment example according to FIG. 2, the surgical navigation system 60 is implemented for working with electromagnetic radiation. Therefore, said system comprises an EM field generator 74 generating an electromagnetic field 75. A plurality of such EM field generators 74 are typically provided. The holding device 1 according to the present embodiment example (FIG. 2) therefore in turn comprises a receiver 70 for communicating with the surgical navigation system 60 and comprising a plurality of Hall-effect sensors 74a, 74b, 74c, 74d, 74e, 74f, 74g (altogether labeled as 74) according to the present embodiment example. One such Hall-effect sensor 74 is provided in each arm segment 10 through 22. Each Hall-effect sensor 74 is connected to the corresponding processor unit 74a-c of the control unit 64 via the BUS system 62, so that each arm segment 10 through 22 can autonomously determine whether said segment is present in the navigated field. According to FIG. 2, all arm segments 10 through 22 are present within the electromagnetic field 75, wherein only half of the arm segment 10 is present within the field.

With respect to the Hall-effect sensors 74, the same description as for the IR photodiodes 72 substantially applies, and the holding device 1 is provided for determining on the basis of the signals received from the Hall-effect sensors 74 whether said device is present in a navigated environment and correspondingly changing into a navigation mode.

FIGS. 3 and 4 again schematically show the construction of the holding device 1 and the periphery, wherein FIG. 3 substantially corresponds to the embodiment example from FIG. 1 and the holding device according to FIG. 4 comprises further additional elements.

Figure 3:
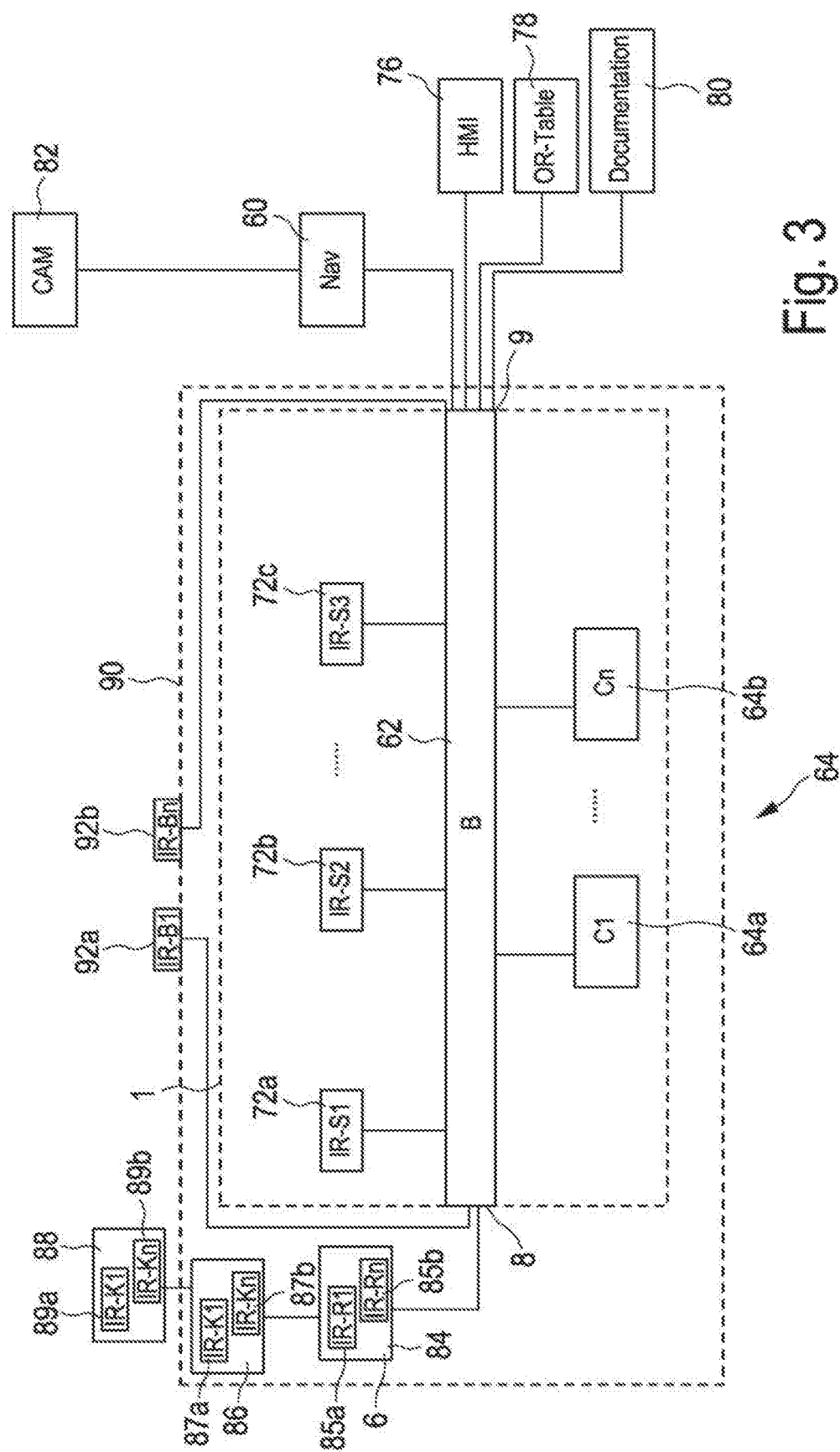
FIG. 3 A further embodiment of the holding device according to the invention.

The holding device 1 is shown in dashed lines in FIG. 3 and the BUS system 62 runs in the interior thereof from the proximal interface 9 to the distal interface 8. The BUS system 62 is coupled to the individual processor units 64a, 64b of the control unit 64 and the IR photodiodes 72a, 72b, 72c. The holding device 1 is connected by wire to a server of the surgical navigation system 60 at the proximal interface 9 in order to receive or forward data in this manner. The holding device 1 is further coupled to a foot pedal 76 via the proximal interface 9, by means of which all joints 11-23 can be released, so that the pose of the holding device 1 can be adjusted altogether. The holding device 1 is further coupled to the operating table 78 via the interface 9 and also connected to a documentation system 80. The documentation system 80 serves for documenting an operation performed in the operating room. The navigation system 60 in turn is connected to a computer 82 and receives CAM data from the same, said data serving for aligning the holding device 1.

The holding device 1 is coupled to an attached device 6 at the distal interface 8 implemented here as a robot unit 84. The robot unit 84 comprises one or more actuators serving for actuating a kinematic device 86 coupled to the robot unit 84. The kinematic device 86 in turn receives a medical instrument 88 such as an endoscope, a biopsy needle, or the like. A sterile bag 90 is disposed about the holding device 1 and the robot unit 84 and the kinematic device 86. For improved communication between the holding device 1 and the surgical navigation system 60, the sterile bag 90 is also equipped with corresponding IR photodiodes 92a, 92b, each connected to the interfaces 8, 9. The robot unit 84 also comprises two IR photodiodes 85a, 85b. The same applies in the present embodiment example to the kinematic device 86 comprising two IR photodiode 87a, 87b and to the instrument 88 comprising two IR photodiodes 89a, 89b. In this manner, the individual attached devices 6, 86, 88 can also receive data and information in turn from the surgical navigation system 60 and process accordingly. To the extent that the kinematic device 86 does not comprise a dedicated control unit, for example, the data is forwarded to the BUS system 62, via which said data can then be processed by means of the control unit 64.

According to FIG. 4, the holding device 1 is shown again, wherein the sterile bag 90 is omitted for simplicity. Identical elements are labeled with the same reference numeral, so that reference is made again to the above description of FIG. 3.

The holding device 1 shown in FIG. 4, in addition to the elements previously described with reference to FIG. 3, comprises angle sensors, labeled altogether as 94 disposed in each joint 11 through 23 and measuring a rotational orientation of each joint 11 through 23. The angle sensors 94 are connected to the control unit 64 via the BUS system 62. The holding device 1 further comprises 3D magnetometers 96, one 3D magnetometer is in turn disposed in each arm segment 10 through 22, so that the pose of the holding device 1 can be determined on the basis of the data of the angle sensors 94 and the 3D magnetometers 96. The determining of the pose of the holding device 1 is performed by the control unit 64. The determined pose is preferably forwarded via the BUS system to the interface 9 and from there to the navigation system 60.

On the basis of the pose determined by means of the angle sensors 94 and on the basis of the pose determined by means of the 3D magnetometer, a deviation of said poses, namely the absolute and relative poses, can be determined. The pose determined by means of the 3D magnetometer deviates from the pose determined by means of the angle sensors 94, as the electromagnetic field comprises an error. The error can be determined by comparing said two poses. On the basis of said error, an error correction can also be performed with respect to other objects present in the electromagnetic field, particularly such as surgical devices. The accuracy of the surgical navigation is thereby substantially improved.

It is further preferable that the holding device 1 comprises one or more acceleration sensors 98, one or more gyroscopes 100, a microphone 102, and one or more photo sensors 104. The acceleration sensors 98, the gyroscopes 100, the microphone 102, and the photo sensors 104 are also coupled to the control unit 64 via the BUS system. It is therefore immaterial in which of the arm segments 10 through 22 the individual sensors are disposed. The acceleration sensors 98 are preferably provided in each segment 10 through 22, and the same applies to the gyroscope 100. The photo sensor and microphone 102, 104 are preferably disposed in the last arm segment 22. The microphone particularly serves for voice recording and the control unit 64 comprises a corresponding voice recognition software program, so that spoken commands from an operator can be translated by means of the control unit 64 into actuating signals for the holding device 1, the robot unit 84, and/or the kinematic device 86. The photosensor or sensors 104 can be used for providing a gesture control for the holding device 1 and/or for taking screenshots of an operating room situation and transmitting the same to the documentation system 80 for documentation purposes.

As can also be seen in FIG. 4, the holding device 1 is equipped with a memory unit 110, potentially implemented in a decentralized manner, having one part in each arm segment 10 through 22. The memory unit 110 is coupled to the control unit 64. The memory unit 110 comprises a plurality of regions. Configurations of the holding device 1, operating room setups from joint angles, connected devices 6, etc. are preferably stored in one region 112. For example, particular poses used for particular standard operations are stored in advance. The control unit is preferably implemented for comparing a particular pose of the holding device to one of the stored poses in the memory unit 112 and for outputting a corresponding signal as to whether the desired pose (the stored pose) has been achieved.

The memory unit 110 further comprises a region 114 in which potential interactions and use profiles for the interaction between a user and the holding device 1 are stored. Stored here, for example, is whether the holding device 1 may be displaced via manual actuation or not in a navigation mode of the holding device 1. Various maximum values for angular velocities in joints are also provided here, for example for the navigation mode and for the operator mode.

In a further memory area 116, communication commands and internal states are stored and then apply when the holding device 1 is connected to the operating table. For example, the acceleration sensor 98 can be used in such a case for capturing a motion of the operating table and outputting the same via the BUS system 62 to the control unit 64 and/or to the surgical navigation system 60.

In a further memory area 118, communication commands and internal states are stored and then apply when the navigation system is connected. The particular conditions for a navigation mode are saved in particular in said memory area 118. If it is determined that the holding device 1 is present in the navigated environment, profiles are loaded from said memory area 118. Further memory areas 120 can be provided and can store particular application case, particular profiles, and the like. Said cases can also be defined by a user, for example via an interface saved on a conventional PC.

A holding device 1 in the form of a holding arm is shown in a side view according to FIG. 5. Identical and similar elements are labeled in turn with identical reference numerals, so that full reference is made to the above description.

The holding device comprises a base 3 at the proximal end 2. The base 3 according to the present embodiment example is implemented as a standard rail of an operating table (the operating table is not shown in FIG. 1). The first arm segment 10 forms the proximal end 2 and comprises a clamping jaw 24 by means of which the holding device 1 can be fixed to the base 3. A power switch 26 is further provided on the arm segment 10 for switching on the entire holding device 1, two connectors 28a, 28b of the interface 9 by means of which the holding device is supplied with power and data, such as actuating signals and the like, and an emergency stop switch 30.

Figure 6:
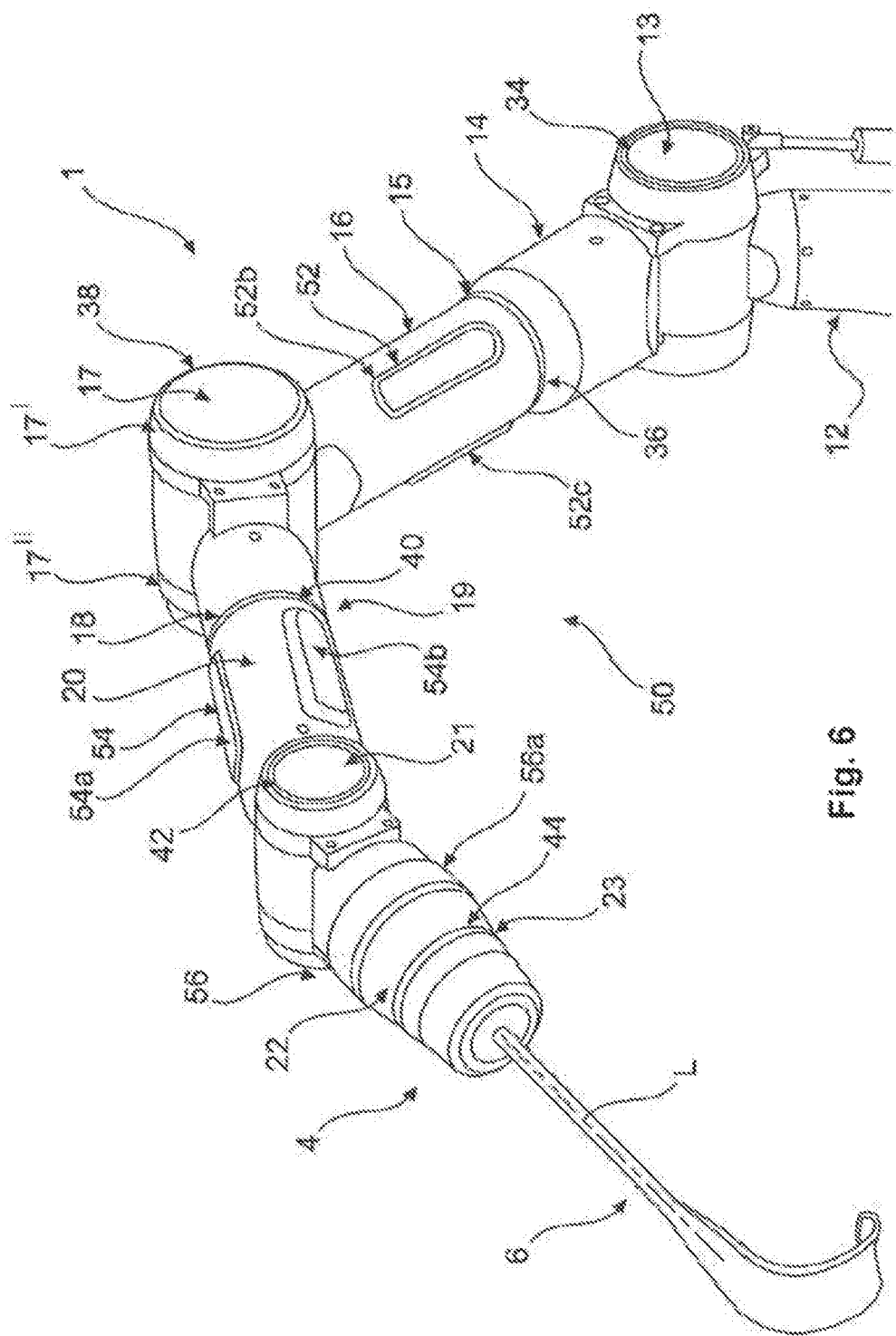

The holding device 1 comprises a display unit 32, 34, 36, 38, 40, 42, 44 at each joint 11, 13, 15, 17, 19, 21, 23, each provided for displaying a status of the holding device and/or of an attached device 6 (cf. FIGS. 2, 3, and 6).

The display units 32, 34, 36, 38, 40, 42, 44 according to said embodiment example are substantially annular in shape. The central axis from each ring runs substantially coaxially to each axis of rotation of the joint 11, 13, 15, 17, 19, 21, 23. While one single ring is provided for each of the joints 11, 15, 19, 23, two opposing rings are provided for each of the joints 13, 17, and 21. The two rings are provided at the front and rear joint segments 17', 17" (labeled with reference numerals as examples only in FIG. 6). Each display unit 32, 34, 36, 38, 40, 42, 44 can always be detected in every position of the holding device 1.

According to the present embodiment example (cf. FIGS. 1 and 6), the holding device 1 further comprises an operator control device 50. By means of the operator control device 50, the holding device 1 can be brought into a desired pose, wherein the operator control device 50 is set up for releasing the associated joint 11, 13, 15, 17, 19, 21, 23 when contact is made between a user and one of the seven arm segments 10, 12, 14, 16, 18, 20, 22. To this end, the operator control unit 29 according to the present embodiment example comprises three contact segments 52, 54, 56, wherein each contact segment 52, 54, 56 is disposed on different arm segment 16, 20, 22. A contact segment 52 is thus disposed on an arm segment 16, a contact segment 54 is disposed on the arm segment 20, and a contact segment 56 is disposed on the arm segment 22. Each contact segment 52, 54, 56 comprises separate contact elements 52a, 52b, 52c, 54a, 54b, 54c, and 56a. The individual contact elements are implemented as touch-sensitive surfaces, so that one or more associated joints are released upon contact between a user and a corresponding contact means.

According to the present embodiment example, three contact elements 52a, 52b, 52c, 54a, 54b, 54c are implemented on each of the arm segments 16 and 20, an annular contact element 56 is disposed on the arm segment 22 and rotatable about the central axis thereof in order to influence functions at an interface to an attached device mounted at the distal end 4.

The association of the individual joints 11, 13, 15, 17, 19, 21, 23 is regulated as follows according to the present embodiment example: upon contact between a user and the arm segment 16, that is, the contact elements 52a, 52b, 52c of the contact segment 52, the joints 15, 13, and 11 are released. A user can now influence three degrees of freedom; this is a scope easily mastered by hand and in which the holding device can be manually brought into a desired pose. If a user makes contact with the arm segment 16, and if the joints 15, 13, and 11 are released, then it is preferably provided that the corresponding display units 32, 34, 36 indicate said releasing according to the embodiment example of FIGS. 1 and 2, that is, by illuminating the ring.

Upon contact between the arm segment 20, that is, the contact segment 54 and particularly the contact means 54a, 54b, 54c, the joints 19 and 17 are released. It is correspondingly preferably provided that the display units 36, 38 indicate the same. Finally, upon contact between the arm segment 22, that is, the contact segment 56 and particularly the contact element 56a, the joints 21 and 23 are released, and said state is preferably indicated by means of the display units 42, 44.

It should be understood that the holding device 1 of the preceding embodiment examples (FIG. 1 through 4) can comprise such an operator control device 50, even if not shown for purposes of clarity.

With reference to FIG. 6, an attached device 6 in the form of a retractor or spreader is received at the distal end 4. One or more force sensors are disposed at the interface at the distal end 4 at which the retractor 6 is received, by means of which a tensile force acting in the direction of the longitudinal axis L can be determined. Corresponding moments at the interface about the longitudinal axis L and perpendicular to the same can preferably also be determined by means of said sensors. The display unit 44 is set up for indicating said status of the attached device 6 and particularly for indicating whether a particular force lies within predefined limits. In operations there is a risk that a retractor 6 has too great a force applied for a longer period of time, whereby the tissue retracted away from the operating field is negatively influenced. By measuring said force and determining whether said force lies within predefined limits, said problem can be reduced or prevented.

Figure 7A:
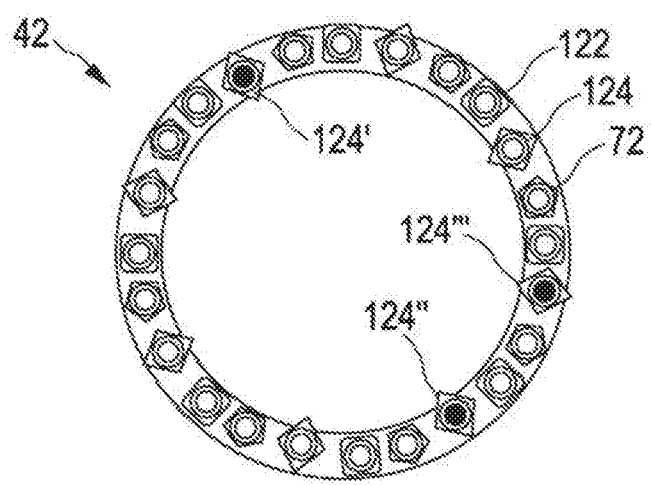
Figure 7B:
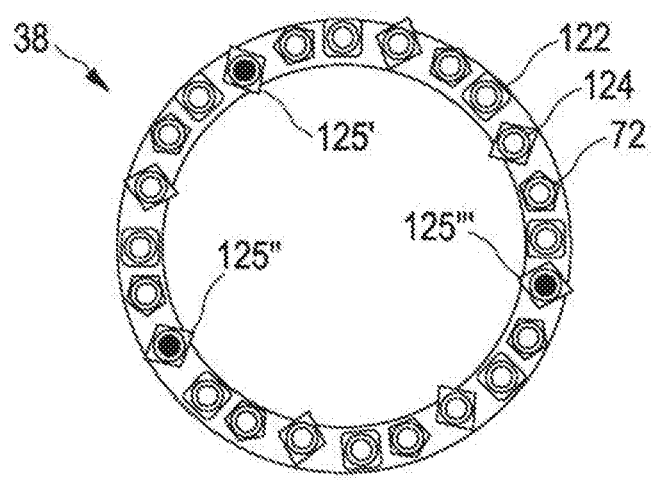
Figure 7C:
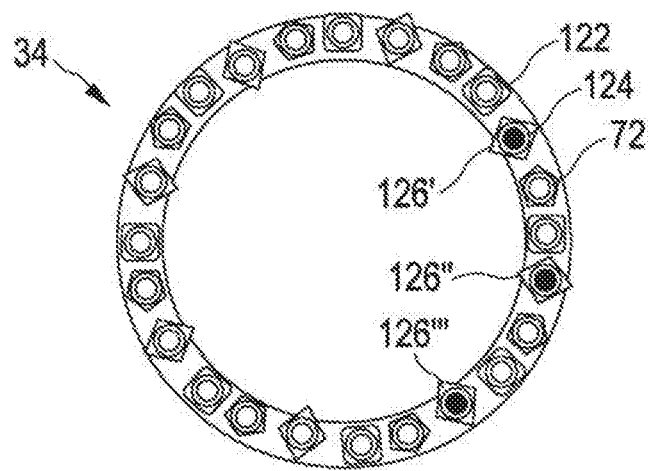

FIGS. 7a through 7c illustrate how the holding device 1 can communication with a surgical navigation system 60 implemented for receiving infrared radiation via the display units 32 through 44. The display units 34, 38, and 42 shown in FIG. 7a through 7c are annular in design and comprise a plurality of elements disposed in a ring. LEDs 122 emitting light in the visible range are each shown having a rectangular border. An element having a rhombic border indicates an IR LED 124 and an element having a pentagonal border indicates an IR photodiode 72. Said element are alternatingly disposed annularly.

The dark coloring of three elements each in FIGS. 7a through 7c indicates that three IR LEDs 124', 124'', 124''' illuminate in the display unit 42, while the remaining IR LEDs 124 in FIG. 7a do not illuminate. The three IR LEDs 124', 124'', 124''' in FIG. 7 a thereby form a unique pattern.

The same applies to the display unit 38 shown in FIG. 7b. There the three IR LEDs 125', 125'', 125''' illuminate and also form a unique pattern, different from the pattern of the three IR LEDs 124', 124'', 124''' from FIG. 7a.

The display unit 34 also comprises LEDs 122, IR LEDs 124, and IR photodiodes 72. On the display unit 34 according to FIG. 7c, the three IR LEDs 126', 126'', 126''' illuminate. By illuminating, said LEDs in turn form a unique pattern different from the pattern of the display units 38 and 42. It is thereby possible that a surgical navigation system uniquely identifies the individual joints at which the display units 34, 38, 42 are provided, namely the joints 13, 17, and 21, and thereby can detect the pose of the holding device 1 on the basis of the IR emission.

It can simultaneously be provided that each LED emitting light in the visible range and disposed adjacent to a corresponding IR LED 124', 124'', 124''', 125', 125'', 125''', 126', 126'', 126''' also illuminates. It is thereby possible for a user to detect in which pattern the corresponding display unit 34, 38, 42 emits IR radiation.

Figure 8A:
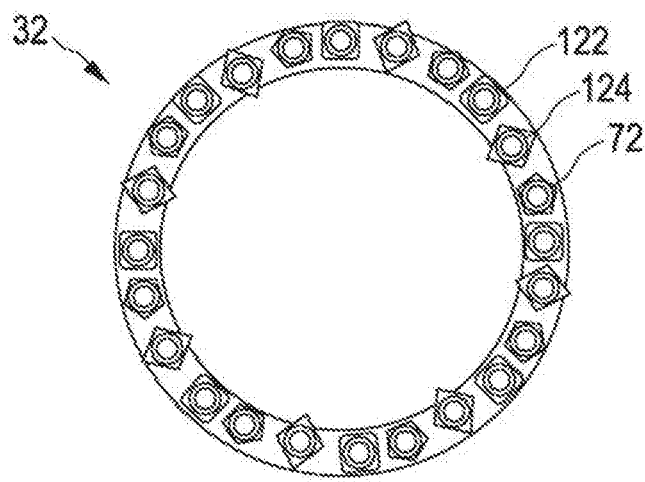
Figure 8B:
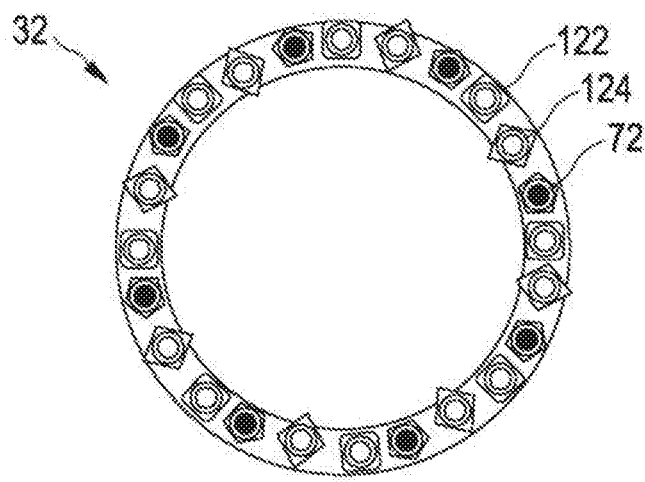
Figure 8C:
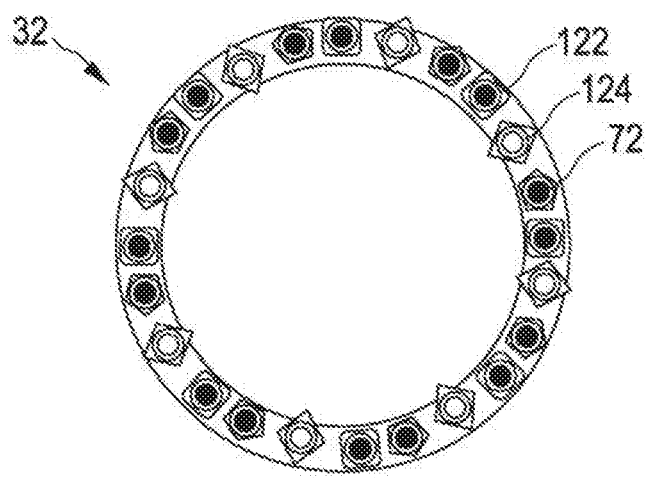

FIGS. 8a through 8c, in contrast, each illustrate the same display unit, simply labeled as 32, in three different states. The elements having rectangular borders are again LEDs emitting light in the visible wavelength range, and the elements having a rhombic border are IR LEDs, and the elements having pentagonal borders are IR photodiodes. In the state shown in FIG. 8a, none of the elements 122, 124, 72 are active. FIG. 8b shows that the display unit 32 receives an IR signal of the surgical navigation system 60, particularly an IR flash. The IR photodiodes 72 are active. FIG. 8c shows an embodiment example modified therefrom, wherein the LEDs 122 emitting light in the visible wavelength range illuminate simultaneously when the IR photodiodes 72 receive a signal. Alternatively, it can be provided that the LEDs 122 emitting light in the visible wavelength range change color. The user thereby receives direct optical feedback as to whether the holding device 1 is receiving IR signals of the surgical navigation system. Safety is thereby further improved.

Figure 9:
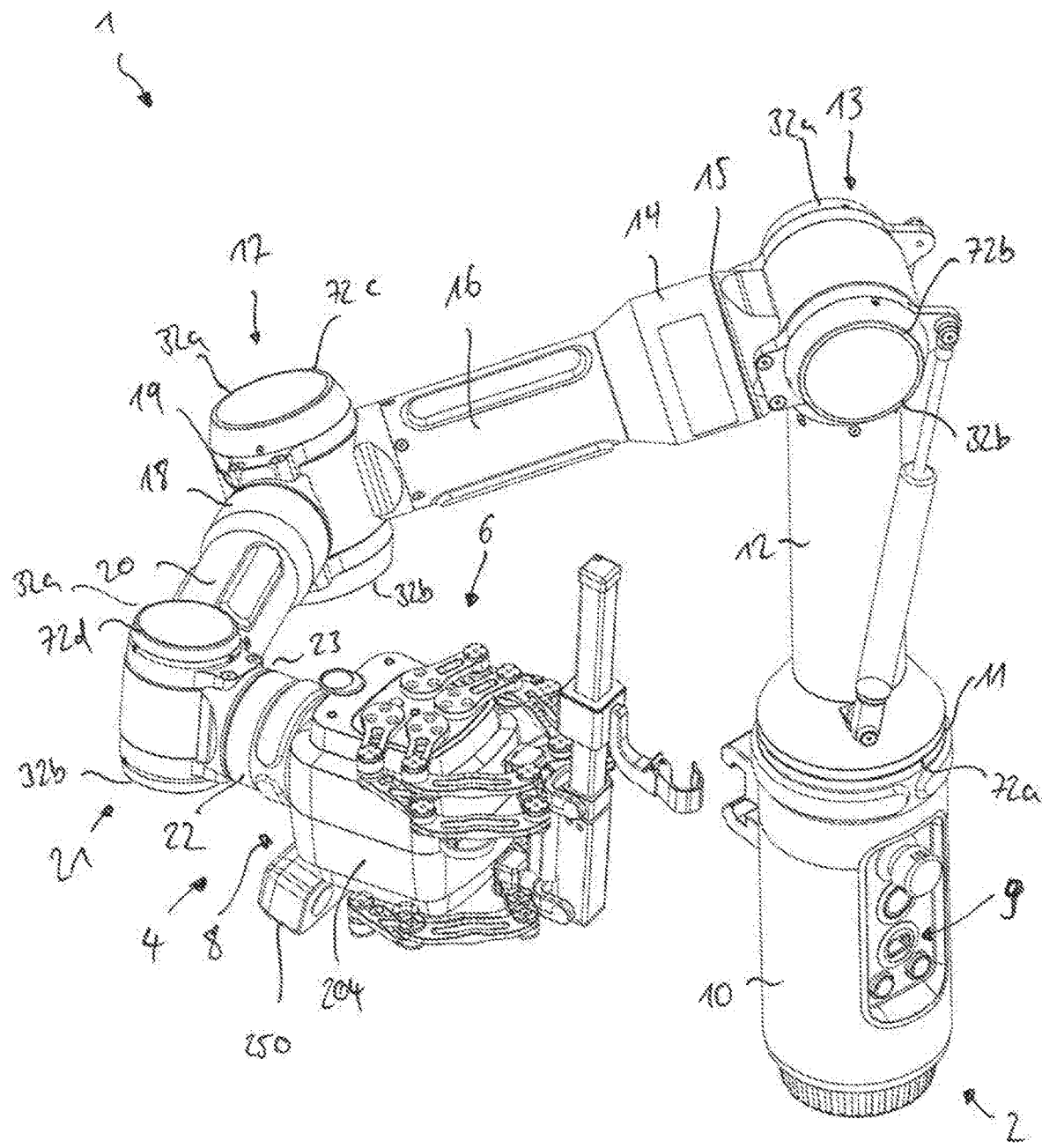
Figure 10:
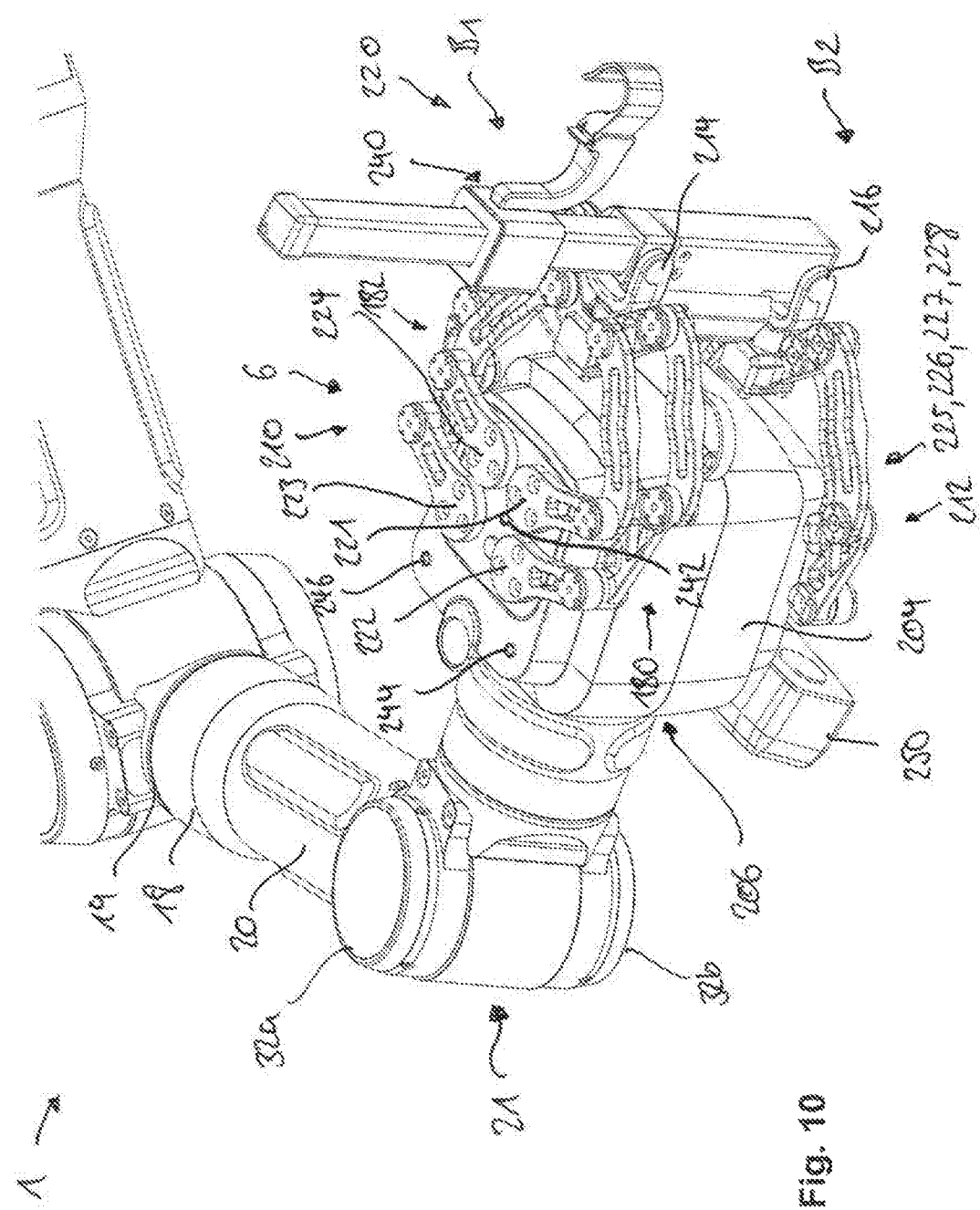
Figure 11:
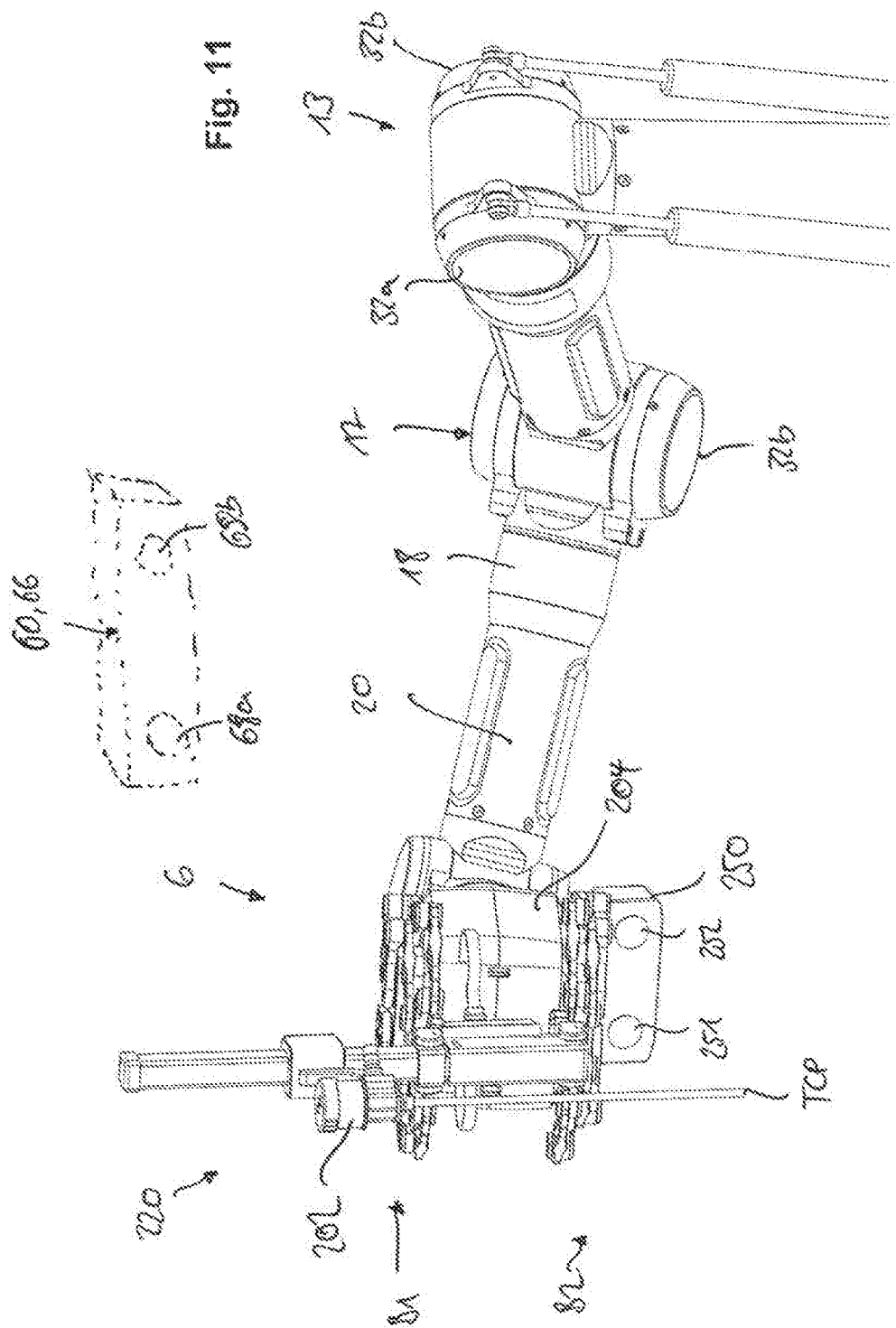
Figure 12:
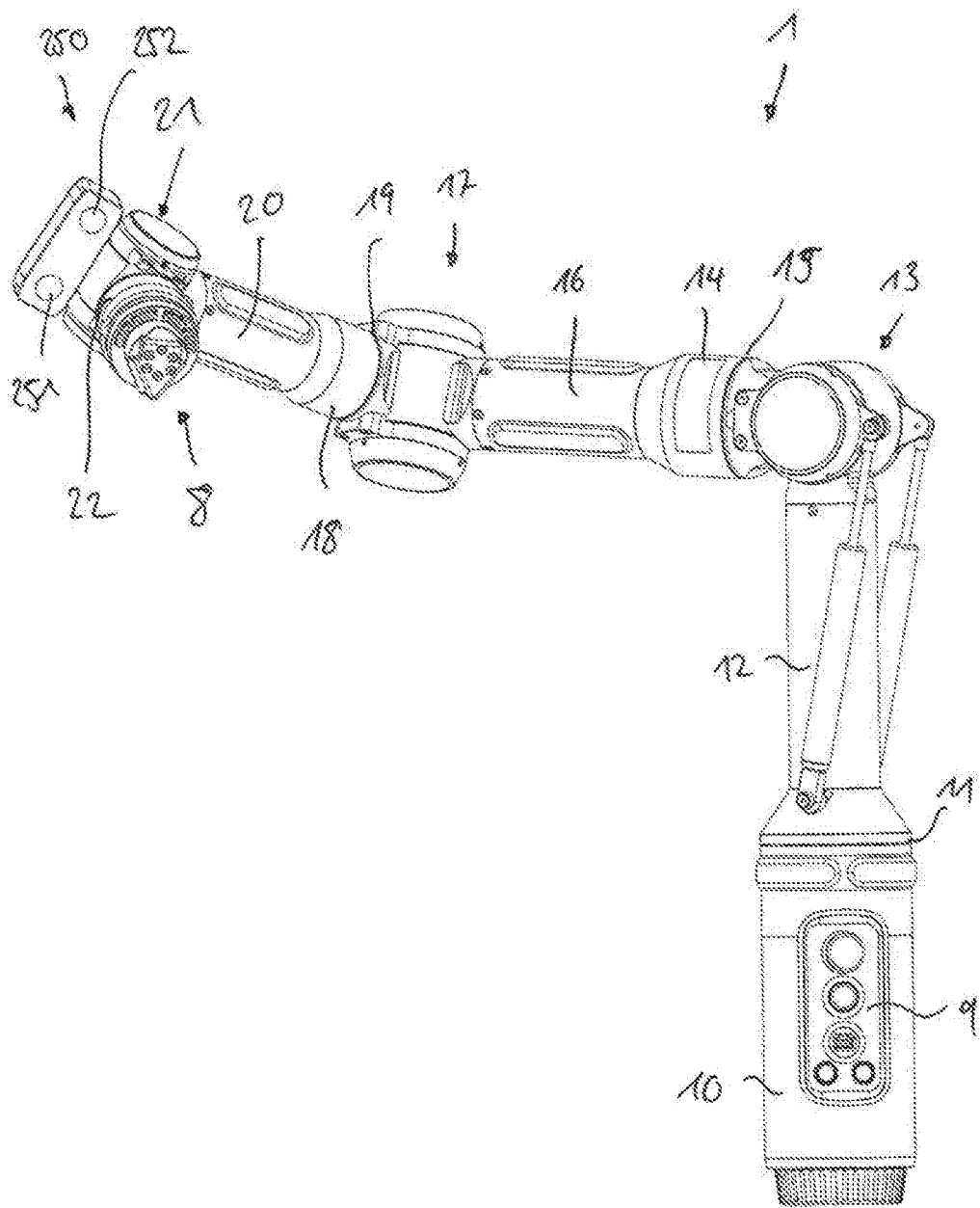

FIGS. 9 through 12 below show further embodiment examples of the holding device, including a robotic attached device disposed thereon (FIGS. 9-11). FIG. 12 shows a further embodiment example, wherein the robotic attached device is omitted in FIG. 12, even though said device can be present.

Although the surgical navigation system 60 is not always shown in FIGS. 9 through 12, it should be understood that said system is present and in this respect reference is made particularly to FIG. 1.

Identical and similar elements are labeled with identical reference numerals to those in the first embodiment examples in the embodiment examples according to FIGS. 9 through 12, so that full reference is made to the description above. The differences to the first two embodiment examples are particularly emphasized below.

According to FIG. 9, the holding device 1 comprises arm segments 10, 12, 14, 16, 18, 20, 22 and joints 11, 13, 15, 17, 19, 21, 23, as previously described with reference to the preceding embodiments.

The infrared sensors 72a, 72b, 72c, 72d are integrated in LED rings, as previously described with reference to FIGS. 7a through 8c. Said rings are particularly disposed about the pivot axes 13, 17, and 21. Two such LED rings implemented as display units 32a, 32b are thereby disposed about the pivot joints 13, 17, 21 at opposite sides of the approximately barrel-shaped joint body. The LED rings of the display unit 32a, 32b are thus visible from each pose and form a line of sight with the navigation camera 68a, 68b of the surgical navigation system 66.

The robotic attached device 6 is removably disposed at the distal interface 8 of the holding device 1. The robot attached device and particularly the kinematics thereof are described in the German patent application DE 10 2017 111 296, the disclosed content of which is hereby incorporated in full.

The robotic attached device 6, implemented here as a surgical manipulator device, is provided for receiving an endoscope 202, for example (cf. FIG. 11). The attached device 6 comprises a housing 24 having an interface 206 (not visible in the figures, as said interface is connected to the distal interface 8), by means of which the attached device 6 is coupled to the distal interface 8 of the holding device 1. With respect to the interface, therefore, reference is made to the German patent application DE 10 2017 111 296.

The attached device 6 further comprises a frame in the interior enclosed by the housing 204. The frame defines the structure of the attached device 6. The frame cannot be seen in FIGS. 9, 10, 11, and 12, because said frame is enclosed by the housing 204.

A first suspension arm arrangement 210 and a second suspension arm arrangement 212 are supported on the frame. The first suspension arm arrangement 210 is displaceable in a first motion plane and the second suspension arm arrangement is displaceable in a second motion plane. The motion planes of the suspension arm arrangement 210, 212 are parallel to each other and cannot be tilted relative to each other.

The first suspension arm arrangement 210 connects the frame to a first mount 214 and the second suspension arm arrangement 212 connects the frame to a second mount 216. By means of the mounts 214, 216, an instrument receiving device 220 is attached to the attached device 6. The first suspension arm arrangement 210 is coupled to the frame at four lever pivot points 221, 222, 223, 224 of the first suspension arm arrangement 210, and the second suspension arm arrangement 212 is coupled to the frame at four lever pivot points 225, 226, 227, 228 of the second suspension arm arrangement 212. The first lever pivot point 221 comprises a first axis of rotation, the second lever pivot point 222 comprises a second axis of rotation, the third lever pivot point 223 comprises a third axis of rotation, and the fourth lever pivot point 224 comprises a fourth axis of rotation. The four lever pivot points 225, 226, 227, 228 of the second suspension arm arrangement 212 are labeled as the fifth lever pivot point, sixth lever pivot point, seventh lever pivot point, and eighth lever pivot point. In said embodiment example, the four lever pivot points 221, 222, 223, 224 of the first suspension arm arrangement 210 comprise common axes of rotation with the four second lever pivot points 225, 226, 227, 228 of the second suspension arm arrangement 212. Altogether, the first and second suspension arm arrangements 210, 212 are implemented identically and mirror-symmetrically. This can be seen particularly well in FIGS. 10 and 11.

The first suspension arm arrangement 210 comprises first and second arm segments 180, 182, in turn identical and mirror-symmetrical to each other. The second suspension arm arrangement 212 correspondingly comprises first and second arm segments, in turn identical and mirror-symmetrical to each other, even if said segments are not labeled with reference numerals in the figures.

Each of the arm segments 180, 182 comprises two parallelograms, namely a first parallelogram, a second parallelogram, a third parallelogram, and a fourth parallelogram. The second lever pivot arrangement comprises corresponding parallelograms.

The first suspension arm arrangement 210 comprises a first lever, a second lever, a third lever, and a fourth lever, the rotary axes thereof each being the axes of rotation. In a corresponding manner, the second suspension arm arrangement 212 comprises a fifth lever, a sixth lever, a seventh lever, and an eighth lever, the rotary axes thereof also being the four axes of rotation indicated. All of the levers are connected to a suspension arm on the output side. The first and second levers are connected to a first suspension arm, and the third and fourth lever and connected to a second suspension arm on the output side. The fifth and sixth levers of the second suspension arm arrangement are connected to a third suspension arm on the output side, and the seventh and eighth levers of the second suspension arm arrangement 212 are connected to a fourth suspension arm on the output side. The first suspension arm and the frame thus jointly form a first parallelogram. The other parallelograms are formed correspondingly.

The first suspension arm arrangement 210 further comprises a first bar, a second bar, a third bar, and a fourth bar. The second suspension arm arrangement comprises corresponding fifth through eighth bars. The first and second bar connect the first suspension arm to the first mount 214 in an articulated manner, and the third and fourth bar connect the second suspension arm to the first mount 214 in an articulated manner. In a corresponding manner, the bars of the second suspension arm arrangement 212 connect the suspension arms to the second mount 216.

A Cardan joint is further provided at the mounts 214, 216 in order to allow different pivoting of the levers and thus different positioning of the mounts in the motion planes B1, B2.

The instrument receptacle 220 further comprises a linear guide 240 allowing displacement of the instrument 202 perpendicular to the motion planes B1, B2 or diagonal thereto.

The attached device 206 in the present embodiment example further comprises a receiver 242, particularly an IR photodiode, for receiving electromagnetic radiation of the surgical navigation system 60. To this end, the receiver 242 is connected to a robot control unit provided within the housing 204. The receiver transmits signals to the robot control unit on the basis of received electromagnetic signals of the surgical navigation system 60. If the robot control unit then detects that the received electromagnetic radiation was transmitted by a surgical navigation system 60, then the robot control unit switches to a navigation mode of the attached device 6. In said navigation mode, for example, it can be provided that the receiver 242 continuously waits for signals, or that particular motions of the first and second suspension arm arrangement 210, 212 are allowed or prevented. In the navigation mode of the attached device 6, it can also be provided that said device transmits electromagnetic radiation by means of transmitters 244, 246 in order to wirelessly transmit a particular status of the attached device 6, such as the pose thereof or the like, to the surgical navigation system by means of electromagnetic radiation. The transmitters 244, 246 can further be used for providing the identity of the attached device 6, so that the surgical navigation system 60 can perceive the attached device 6. Particularly for surgical navigation systems operating by means of navigation cameras and infrared radiation, it is typical that the surgical navigation system can only detect objects emitting infrared radiation themselves. So-called trackers are typically installed to this end and reflect infrared radiation emitted by the surgical navigation system 60. If the attached device 6, in contrast, comprises active transmitters 244, 246, then the installing of additional trackers is not necessary, as the functionality thereof can be assumed by the transmitters 244, 246. The transmitters 244, 246 can then also blink, for example, in order to transmit particular information to the surgical navigation system 60 by means of said blinking.

It is further provided according to the present embodiment (FIGS. 9-11) that the attached device 6 comprises a navigation camera 250. The navigation camera 250 of the attached device 6 can be seen particularly well in FIG. 11. The navigation camera 250 is disposed at the lower region of the attached device 6, wherein "lower" refers here to a typical alignment of the attached device 6. It is, of course, also possible that the attached device 6 assumes a different pose and is rotate about the axis thereof, for example.

The navigation camera 250 comprises first and second lenses 251, 252 aimed at the operating field, that is, a tool center point TCP of the surgical instrument 202. It can be provided that the navigation camera 250 is pivotable relative to the attached device 6 and that a corresponding drive is provided to this end. It is thus conceivable and preferable, for example, that when the position of the surgical instrument 202 changes, the navigation camera 250 is also pivoted in order to retain an optimal view of the operating field. The navigation camera 250 can particularly capture the region obscured by the holding device and/or the attached device 6 with respect to a surgical navigation camera 68a, 68b of a surgical navigation system 66. This can also be seen in FIG. 11 as the schematically depicted surgical navigation system 66.

The navigation camera 250 can thus receive the operating field, even if said field is obscured by the holding device 1 and/or the attached device 6 with respect to the surgical navigation system 60. The signals received by the navigation camera 250 can first be forwarded to the attached device 6, from there to the holding device 1 via the interface 206 and the proximal interface 8, particularly to the internal bus system thereof, and then provided by means of the proximal interface 9. It can thereby be provided that the attached device 6 and/or the holding device 1 process the signals received by the navigation camera 250. Such processing can particularly comprise: linking to data indicating the position of the navigation camera 250, reporting on instruments present in the operating field, and the like.

In a further embodiment example (FIG. 12), the navigation camera 250 is disposed on the holding device 1. In the present embodiment example, it is not necessary that the attached device 6 be equipped with a navigation camera. Rather, regardless of the attached device 6 mounted at the interface 8, the operating field can be received by the navigation camera 250 directly connected to the holding device 1. It is also possible to use the navigation camera 250 as an additional navigation camera by means of the holding device 1, without holding a special attached device 6 at the interface 8. This is then particularly advantageous if other devices are disposed in the operating field and partially obscure the operating field with respect to the navigation system 60. The navigation camera 250 can be coupled directly to the internal bus system of the holding device 1 in this case. In the embodiment example shown in FIG. 12, the navigation camera is connected to the next-to-last arm segment 20 and particularly in the region of the joint 21 there. The navigation camera 250 can, however, also be disposed on a last arm segment 22, having the advantage that orienting the navigation camera 250 is thereby more easily achieved.

The invention claimed is:

1. A holding device for holding a surgical mechatronic assistance system and/or a surgical instrument, the holding device comprising:
   a proximal end configured to attach to a base and a distal end configured to receive the surgical mechatronic assistance system and/or the surgical instrument;
   a first arm segment and a second arm segment, the first arm segment being connected to a first joint and the second arm segment being connected to a second joint, each of the first and second joints being releasable or lockable;
   an operator control device for releasing and/or locking the first joint and/or the second joint for placing the holding device in a desired pose;
   a controller for controlling the holding device; and
   at least one receiver for electromagnetic radiation in electrical communication with the controller and configured to transmit signals to the controller based on received electromagnetic signals of a surgical navigation system, wherein:
      the holding device is configured to be operated in a navigation mode and an operator mode,
      in the operator mode, the holding device is configured to be operated manually via an operator control unit,
      in the navigation mode, the holding device is configured to receive commands from the surgical navigation system, and
      the controller is configured to:
         determine, based on the signals transmitted from said at least one receiver, whether the holding device is present in a navigated surgical environment or whether the holding device is not present in the navigated surgical environment, and
         automatically switch the holding device into the navigation mode if it is determined that the holding device is present in the navigated surgical environment, and automatically switch the holding device into the operator mode if it is determined that the holding device is not present in the navigated surgical environment.

2. The holding device of claim 1, wherein the receiver comprises an infrared sensor, a Hall-effect sensor, or a 3D magnetometer.

3. The holding device of claim 1, further comprising at least one transmitter configured to transmit electromagnetic radiation for transmitting signals to the surgical navigation system.

4. The holding device of claim 3, wherein the transmitter comprises an IR light source.

5. The holding device of claim 3, wherein the at least one transmitter is configured to emit a signal if one or more brakes on the first or second joint are opened and/or if the first or second joint is displaced.

6. The holding device of claim 1, further comprising a first display unit disposed on the first joint and a second display unit disposed on the second joint, wherein the first display unit and the second display unit each comprise at least one IR light source and are configured to display at least one status of the holding device and/or a status of the surgical mechatronic assistance system and/or the surgical instrument.

7. The holding device of claim 1, further comprising a navigation camera for capturing an operating field.

8. The holding device of claim 7, wherein the holding device is configured to provide signals captured by the navigation camera to an interface for the surgical navigation system.

9. The holding device of claim 1, further comprising a BUS system, a first mechatronic interface at the proximal end, and a second mechatronic interface at the distal end, wherein the second mechatronic interface is configured to couple to the surgical mechatronic assistance system and/or the surgical instrument.

10. The holding device of claim 1, wherein the at least one receiver is configured to wirelessly receive electromagnetic radiation.

11. A method for communicating between a holding device and a surgical navigation system, the method comprising:
receiving, at the holding device, electromagnetic radiation from the surgical navigation system via a receiver;
transmitting, in response to the reception of the electromagnetic radiation, a signal from said receiver to a controller;
determining, based on the signal transmitted from said receiver to said controller, whether the holding device is present in a navigated surgical environment or whether the holding device is not present in the navigated surgical environment;
automatically switching the holding device into navigation mode if it is determined that the holding device is present in the navigated surgical environment, that the holding device is configured to receive commands from the surgical navigation system; and
automatically switching the holding device into operator mode if it is determined that the holding device is not present in the navigated surgical environment.

12. The method of claim 11, further comprising:
transmitting commands, from the surgical navigation system to the holding device, via the electromagnetic radiation; and
receiving, at the holding device, the commands via the receiver.

13. The method of claim 11, further comprising:
transmitting, from a transmitter of the holding device, electromagnetic radiation for transmitting signals to the surgical navigation system; and
receiving the signals at the surgical navigation system, wherein the signals represent a status of the holding device and/or of an attached device.

14. The method of claim 11, wherein the receiver of the holding device comprises at least one 3D magnetometer and the holding device is disposed in an electromagnetic field of the surgical navigation system, the method further comprising:
determining a relative pose of the holding device relative to the electromagnetic field based on signals transmitted by the at least one 3D magnetometer;
determining an absolute pose of the holding device;
comparing the relative and absolute pose of the holding device; and
determining an error of the electromagnetic field based on the comparison of the relative and absolute poses of the holding device.

15. The method of claim 14, further comprising determining a position of an object present in the electromagnetic field using the determined error.

16. The method of claim 14, wherein determining the absolute pose of the holding device comprises:
determining positions of joints of the holding device; and
calculating the absolute pose based on the positions of the joints.

17. The method of claim 14, wherein determining the absolute pose of the holding device comprises capturing the absolute pose of the holding device via an optical capture unit.

18. The method of claim 11, wherein receiving the electromagnetic radiation from the surgical navigation system via the receiver comprises wirelessly receiving the electromagnetic radiation from the surgical navigation system via the receiver.

19. A holding device for holding a surgical mechatronic assistance system and/or a surgical instrument, the holding device comprising:
a proximal end comprising a first mechatronic interface configured to attach to a base;
a distal end comprising a second mechatronic interface configured to couple to the surgical mechatronic assistance system and/or the surgical instrument;
a BUS system;
a first arm segment and a second arm segment, the first arm segment being connected to a first joint and the second arm segment being connected to a second joint, each of the first and second joints being releasable or lockable;
an operator control device for releasing and/or locking the first joint and/or the second joint for placing the holding device in a desired pose;
a controller for controlling the holding device; and
at least one receiver for electromagnetic radiation in electrical communication with the controller and configured to transmit signals to the controller based on received electromagnetic signals of a surgical navigation system, wherein:
the holding device is configured to be operated in a navigation mode and an operator mode,
in the operator mode, the holding device is configured to be operated manually via an operator control unit,
in the navigation mode, the holding device is configured to receive commands from the surgical navigation system, and
the controller is configured to determine, based on the received signal, that the holding device is present in a navigated surgical environment and to switch the holding device into the navigation mode.

* * * * *